US008211857B2

(12) United States Patent
Stewart

(10) Patent No.: US 8,211,857 B2
(45) Date of Patent: Jul. 3, 2012

(54) PEPTIDE COMPOSITION FOR CANCER TREATMENT BY INHIBITING TRPV6 CALCIUM CHANNEL ACTIVITY

(75) Inventor: John M. Stewart, Sackville (CA)

(73) Assignee: Soricimed Biopharma Inc., Sackville, NB (CA)

( * ) Notice: Subject to any disclaimer, the term of this patent is extended or adjusted under 35 U.S.C. 154(b) by 0 days.

(21) Appl. No.: 12/886,397

(22) Filed: Sep. 20, 2010

(65) Prior Publication Data

US 2011/0071089 A1  Mar. 24, 2011

Related U.S. Application Data

(63) Continuation-in-part of application No. PCT/CA2009/000343, filed on Mar. 18, 2009.

(60) Provisional application No. 61/037,903, filed on Mar. 19, 2008.

(51) Int. Cl.
*A61K 38/17* (2006.01)
*A61K 38/10* (2006.01)
*C07K 14/47* (2006.01)

(52) U.S. Cl. ............................. 514/12; 514/14; 530/300

(58) Field of Classification Search ........................ None
See application file for complete search history.

(56) References Cited

U.S. PATENT DOCUMENTS

| 5,424,286 A | 6/1995 | Eng |
| 6,326,020 B1 | 12/2001 | Kohane et al. |
| 6,534,642 B1 | 3/2003 | Hediger et al. |
| 6,946,475 B1 | 9/2005 | Gray et al. |
| 7,119,168 B2 | 10/2006 | Stewart et al. |
| 7,205,108 B2 | 4/2007 | Wissenbach |
| 7,273,850 B2 | 9/2007 | Stewart et al. |
| 7,485,622 B2 | 2/2009 | Stewart et al. |
| 7,745,588 B2 | 6/2010 | Stewart et al. |
| 2010/0305029 A1 | 12/2010 | Stewart et al. |

FOREIGN PATENT DOCUMENTS

| EP | 1165508 | 6/2004 |
| JP | 10-236963 | 9/1998 |
| WO | 2004/046178 | 6/2004 |

OTHER PUBLICATIONS

Lehen'Kyi, V. et al. "TRPV6 is a Ca2+ entry channel essential for Ca2+-induced differentiation of human keratinocytes." J Biol Chem, 2007, 282(31):22582-22591. eISSN: 1083-351X.
Sternfeld, L. et al. "Identification of tyrosines in the putative regulatory site of the Ca2+ channel TRPV6." Cell Calcium, 2007, 42:91-102. eISSN: 1532-1991.
Bolanz, K. et al. "The role of TRPV6 in breast carcinogenesis." Mol Cancer Ther, Feb. 2008, 7(2):271-279. eISSN: 1538-8514.
Cai, Z. et al., "Solution Structure of BmBKTx1, a New BK.sub.CA.sup.1 Channel Blocker from the Chinese Scorpion *Buthus martensi* Karsch", Biochemistry, vol. 43, No. 13, pp. 3764-3771, 2004.

Christenbury, P., "A Study of the Ecology of *Blarina brevicaudia* in North Carolina and of the Effect of Shrew Toxin on the Liver and Kidneys of Mice". A thesis submitted to the Graduate Faculty of Wake Forest College in partial fulfillment of the requirements for the degree of Master of Arts in the Department of Biology, Aug. 1966.
Dekker, E. et al. "The epithelial calcium channels, TRPV5 and TRPV6: from identification towards regulation", Cell Calcium, vol. 33, pp. 497-507, 2003.
Dufton, M., "Venomous Mammals", Pharmac. Ther., vol. 53, pp. 199-215, 1992.
Ellis, S. et al., "Properties of a Toxin From the Salivary Gland of the Shrew, *Blarina brevicauda*", The Journal of Pharmacology & Experimental Therapeutics, vol. 114, No. 2, pp. 127-137, 1955.
Wissenbach, U. et al. "TRPV6 and prostate cancer: cancer growth beyond the prostate correlates with increased TRPV6 Ca2+ channel expression." Biochem. Biophys. Res. Comm., 2004, 322: 1359-1363.
George, S. et al., "*Blarina brevicauda*", Mammalian Species, No. 261, pp. 1-9, 3 Figures, 1986.
Kita, M. et al., "*Blarina* toxin, a mammalian lethal venom from the short-tailed shrew *Blarina brevicauda*: Isolation and characterization", Proceedings of the National Academy of Sciences of the United States of America, vol. 101, No. 20, pp. 7542-7547, 2004.
Lecchi, P. et al., "The Structure of Synenkephalin (Pro-Enkephalin .sub.1-73) Is Dictated by Three Disulfide Bridges", Biochemical and Biophysical Research Communications, vol. 232, pp. 800-805, 1997.
Martin, I., "Venom of the Short-Tailed Shrew (*Blarina brevicauda*) As an Insect Immobilizing Agent", Journal of Mammalogy, vol. 62, No. 1, pp. 189-192, 1978.
Montell, C., "The venerable inveterate invertebrate TRP channels", Cell Calcium, vol. 33, pp. 409-417, 2003.
Mount Allison University, "Potent Peptide Paralytic Agent", Version 1, Jun. 2003.
Mount Allison University, "Potent Peptide Paralytic Agent", Version 2, Jul. 2003.
Pearson, O., "On the cause and nature of poisonous action produced by the bite of a shrew (*Blarina brevicauda*," Journal of Mammalogy, pp. 159-166, (1942).
Peng, J. et al., "CaT1 Expression Correlates with Tumor Grade in Prostate Cancer", Biochemical and Biophysical Research Communications, vol. 282, pp. 729-734, 2001.
Peng, J. et al., "Human Calcium Transport Protein CaT1", Biochemical and Biophysical Research Communications, vol. 278, pp. 326-332, 2000.
Pohl, M. et. al., "Molecular Cloning of the Helodermin and Exendin-4 cDNAs in the Lizard", The Journal of Biological Chemistry, vol. 273, No. 16, pp. 9778-9784, 1998.
Pucek, M., Chemistry and Pharmacology of Insertivore Venoms, Chapter 3 of Venomous Animals and Their Venoms edited by W. Bucherl, Academic Press, New York—London, pp. 43-50, 1968.
Smart, P., "Shrew Saliva Spells Relief? Prof. Jack Stewart makes breakthrough medical discovery", the argosy, Jan. 16, 2003.
(Author Unknown),"The venom of the shrew maybe the new Botox", National Post, Science Section, Biochemistry, Dec. 20, 2002.

(Continued)

*Primary Examiner* — Ruixiang Li
(74) *Attorney, Agent, or Firm* — Bereskin & Parr LLP; Noel Courage

(57) ABSTRACT

The invention includes an isolated peptide comprising all or part of the amino acid sequence: EGKLSSNDTE GGLCK-EFLHP SKVDLPR (SEQ ID NO: 1), wherein the peptide inhibits calcium channel activity. The peptides of the invention are useful for preventing or treating cancer.

6 Claims, 14 Drawing Sheets

OTHER PUBLICATIONS

Tomasi, T., "Function of Venom in the Short-Tailed Shrew *Blarina brevicauda*", Journal of Mammalogy, vol. 59, No. 4, pp. 852-854, 1978.

Zhuang, L. et al., "Calcium-Selective Ion Channel, CaT1, Is Apically Localized in Gastrointestinal Tract Epithelia and Is Aberrantly Expressed in Human Malignancies", Laboratory Investigation, vol. 82, No. 12, pp. 1755-1764, 2002.

Pigozzi, D. et al. "Calcium store contents control the expression of TRPC1, TRPC3 and TRPV6 in LnCaP prostate cancer cell line." Cell Calcium, 2006, 39: 401-415.

Lehen'Kyi, V. et al. "TRPV6 channel controls prostate cancer cell proliferation via Ca2+/NFAT-dependent pathways." Oncogene, 2007, 26: 7380-7385.

Bodding M., Fecher-Trost C, Flockerzi V. "Store-operated Ca2+ Current and TRPV6 Channels in Lymph Node Prostate Cancer Cells." J Biol Chem, 2003, 278 (51): 50872-50879.

Agnes R.S. et al. "Structure-activity relationships of bifunctional peptides based on overlapping parmacophores and opioid and cholescytokinin receptors." Journal of Medicinal Chemistry, 2006, 49: 2868-2875.

Yamamoto T. et al. "A structure-activity relationship study of combinatorial synthetic approach of C-terminal modified bifunctional peptides that are delt/mu opioid receptor agonists and neurokinin 1 receptor antagonists." Journal of Medicinal Chemistry, Mar. 13, 2008; 51(5): 1369-1376, epub, Feb. 12, 2008.

Lyshchik A. et al. "Cervical lymph node metastases: diagnosis at sonoelastography—initial experience." Radiology, Apr. 2007;243(1):258-67. Epub Feb. 9, 2007.

Vernooij F. et al. "Lymph node recurrence following stage IA vulvar carcinoma: two cases and a short overview of literature." Int J Gynecol Cancer., Mar.-Apr. 2007;17(2):517-20. Epub Feb. 19, 2007.

Aalders, J.G et al. "Endometrial cancer—revisiting the importance of pelvic and para aortic lymph nodes." Gynecol Oncol., Jan. 2007;104(1):222-31. Epub Nov. 28, 2006.

Veness M.J. et al. "Cutaneous head and neck squamous cell carcinoma metastatic to parotid and cervical lymph nodes." Head Neck., Jul. 2007;29(7):621-31.

Ma J. et al. "Retropharyngeal lymph node metastasis in nasopharyngeal carcinoma: prognostic value and staging categories." Clin Cancer Res., Mar. 1, 2007;13(5):1445-52.

Mujoomdar A. et al. "Clinical predictors of metastatic disease to the brain from non-small cell lung carcinoma: primary tumor size, cell type, and lymph node metastases." Radiology, Mar. 2007;242(3):882-8. Epub Jan. 17, 2007.

Wind J. et al. "A systematic review on the significance of extracapsular lymph node involvement in gastrointestinal malignancies." Eur J Surg Oncol., May 2007;33(4):401-8. Epub Dec. 15, 2006.

Stewart, J.M. et al. "A novel peptide inhibitor of TRPV6 shows activity against ovarian cancer in vitro and in vivo." Poster and Abstract presented at TRP Meeting, Sep. 26-27, 2009, Karolinska Institutet, Stockholm.

Stewart, J.M., and Roy, F. "News Release: BioProspecting and Atlantic Cancer Research Institute established formal collaboration to develop early diagnostic for ovarian cancer." BioProspecting NB, Inc. and Atlantic Cancer Research Institute, Oct. 20, 2009.

Fixemer, T. et al. "Expression of the Ca+2-selective cation channel TRPV6 in human prostate cancer: a novel prognostic marker for tumor progression." Oncogene, 2003, 22: 7858-7861.

Wissenbach, U. et al. "Expression of CaT-like, a Novel Calcium-selective Channel, Correlates with the Malignancy of Prostate Cancer." J. Biol. Chem., 2001, 276: 22, 19461-19468.

Schwarz et al. "TRPV6 potentiates calcium-dependent cell proliferation." Cell Calcium, 2006, vol. 39, No. 2, pp. 163-173.

Bodding, M. "TRP proteins and cancer." Cellular Signalling, 2007, 19: 617-624.

Hoenderop, J.G.J. et al. "Epithelial Ca2+ and Mg2+ Channels in Health and Disease." J. Am. Soc. Nephrol., 2005, 16: 15-26.

Lee, W.J. et al. "Calcium transport and signaling in the mammary gland: Targets for breast cancer." Biochim. Biophys. Acta, 2006, 1765: 235-255.

Nilius, B. et al. "Transient Receptor Potential Cation Channels in Disease." Physiol. Rev., 2007, 97: 165-217.

Prevarskaya, N. et al. "TRP channels in cancer. Biochim." Biophys. Acta, 2007, 1772: 937-946.

Prevarskaya, N., et al. "Ion channels in death and differentiation of prostate cancer cells." Cell Death and Differentiation, 2007, 14: 1295-1304.

Prevarskaya, N., et al. "Differential role of TRP channels in prostate cancer." Biochem. Soc. Trans., 2007, 35: 133-135.

Semenova, S. et al. "Endogenous expression of TRPV5 and TRPV6 calcium channels in human leukemia K562 cells." Am. J. Physiol. Cell Physiol., 2009, 296: C1098-C1104. (published on line Mar. 18, 2009, hardcopy in May 2009.).

Thebault, S. et al. "Differential Role of Transient Receptor Potential Channels in Ca2+ Entry and Proliferation of Prostate Cancer Epithelial Cells." Cancer Res., 2006, 66(4): 2038-2047.

Vanden Abeele, F. et al. "Store-operated Ca2+ channels in prostate cancer epithelial cells: function, regulation and role in carcinogenesis." Cell Calcium, 2003, 33: 357-373.

Vriens, J. et al. "Pharmacology of vanilloid transient receptor potential cation channels." Molecular Pharmacology, 2009, 75 (6): 1262-1279. (published online Mar. 18, 2009; in paper journal Jun. 2009.).

Wissenbach, U. et al. "TRPV6." HEP, 2007, 179: 221-234.

FIG. 1
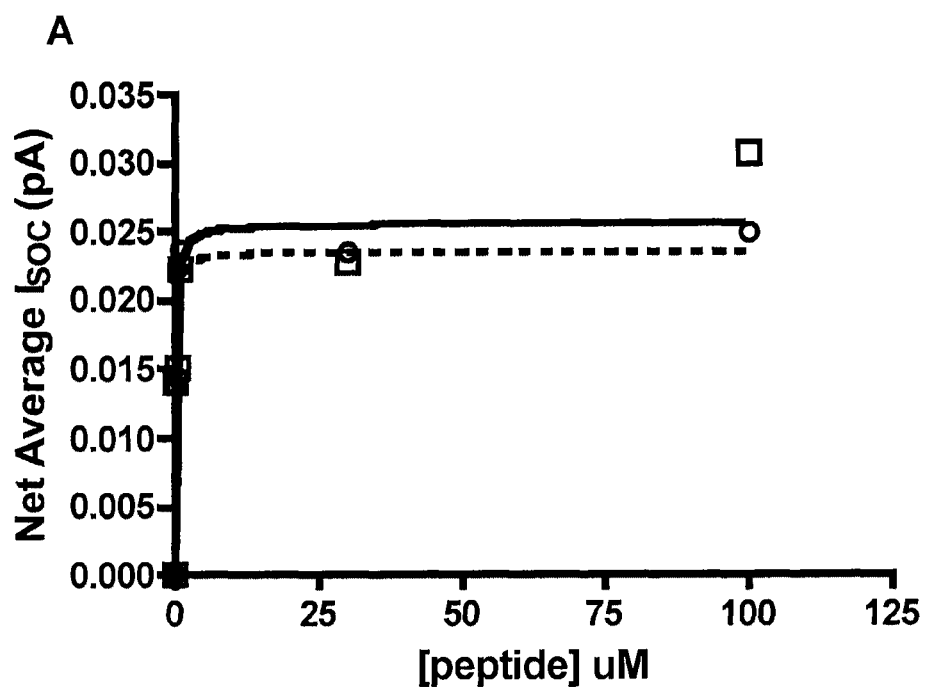
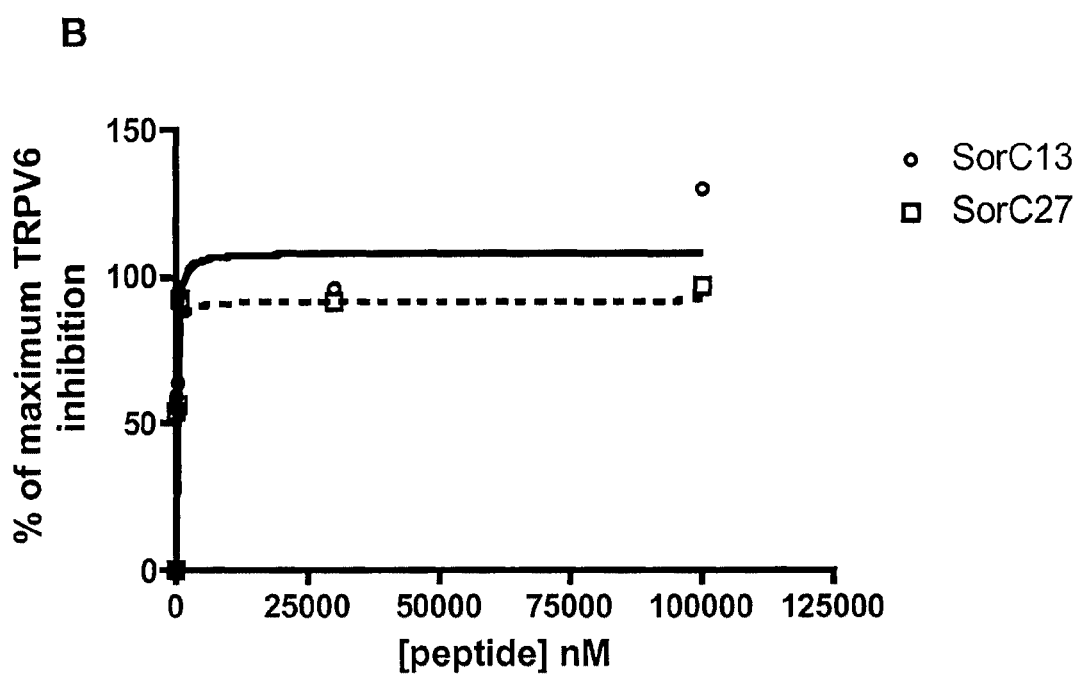
○ SorC13
□ SorC27

FIG. 5
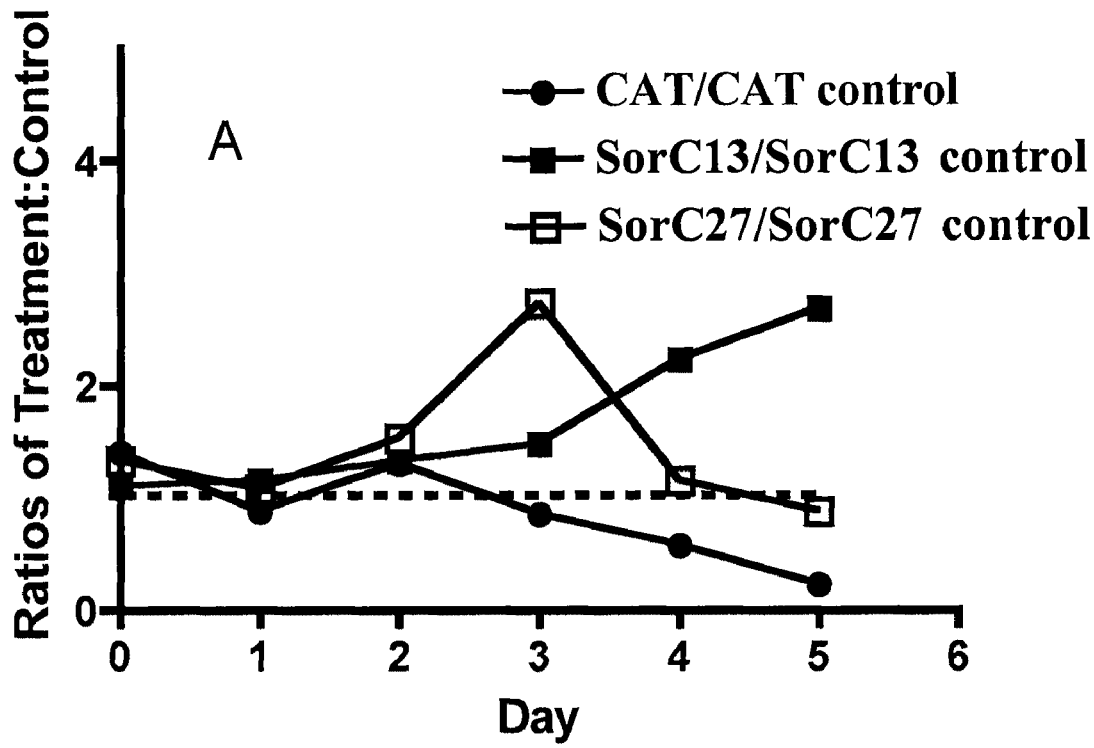
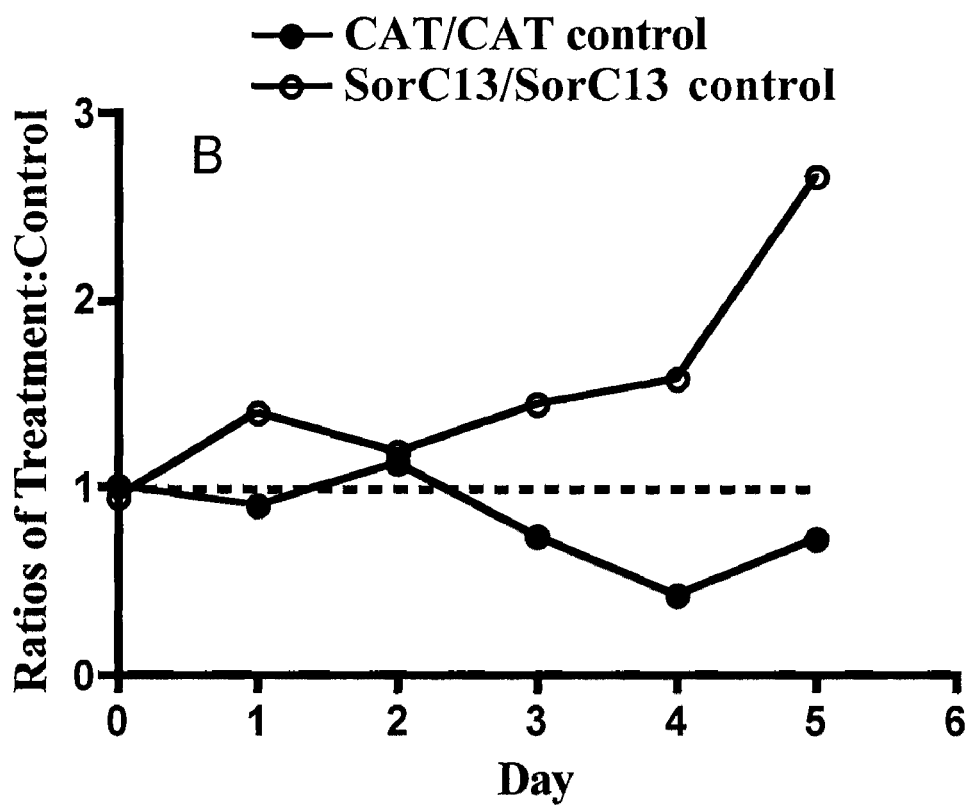

FIG. 10
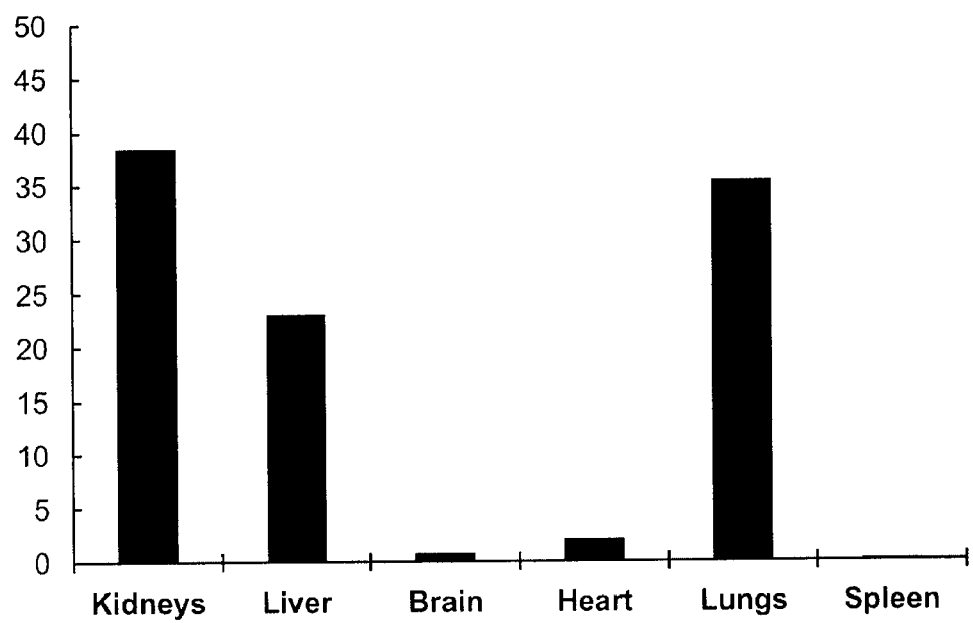
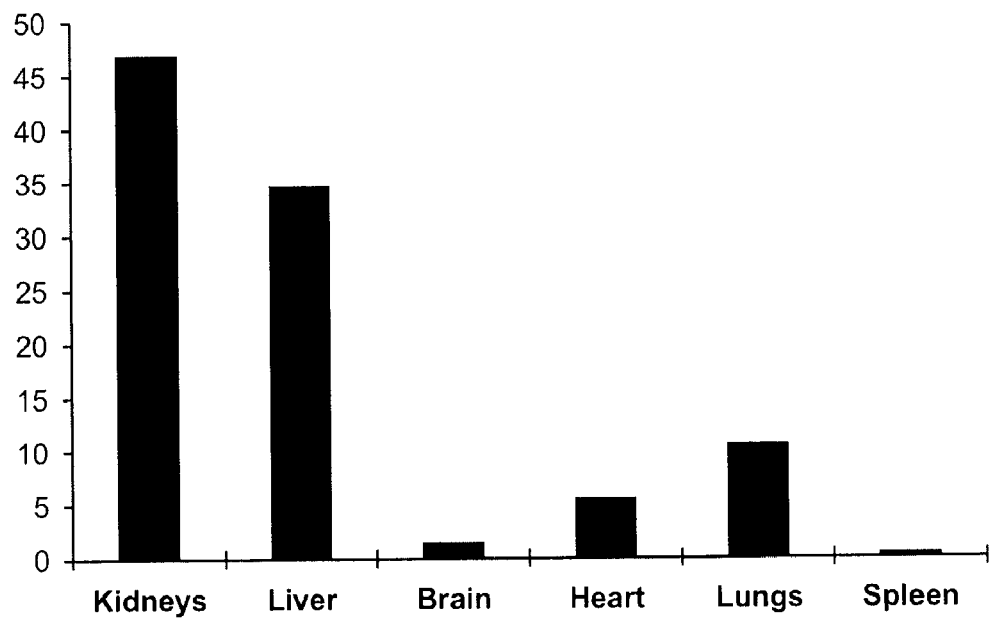

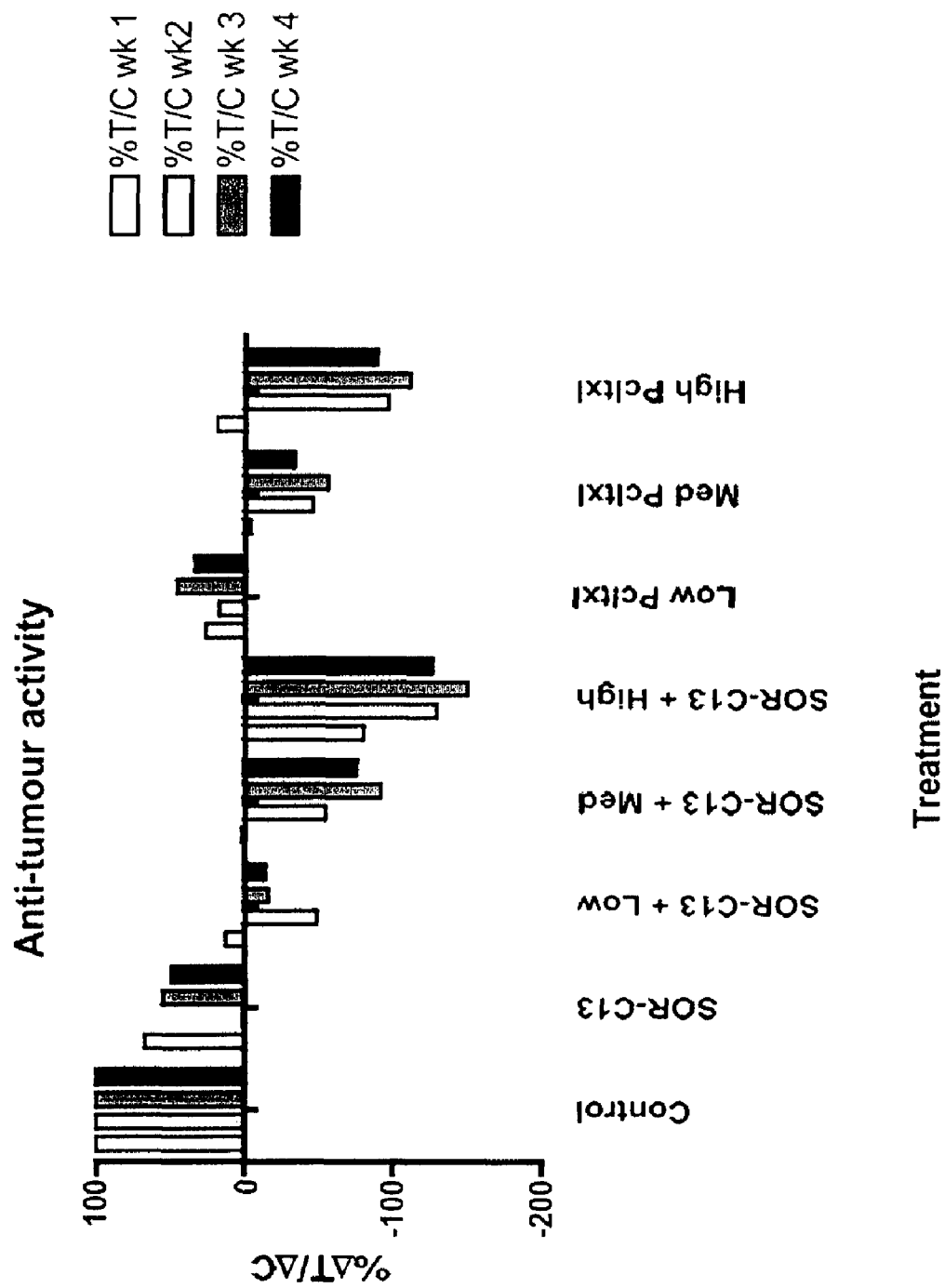

US 8,211,857 B2

PEPTIDE COMPOSITION FOR CANCER TREATMENT BY INHIBITING TRPV6 CALCIUM CHANNEL ACTIVITY

CROSS REFERENCE TO RELATED APPLICATIONS

This application is a continuation-in-part of PCT/CA2009/000343 filed on Mar. 18, 2009, which claims priority from U.S. application No. 61/037,903 filed on Mar. 19, 2008, all of which are incorporated by reference herein in their entirety.

INCORPORATION OF SEQUENCE LISTING

A computer readable form of the Sequence Listing "15309-30_Sequence_Listing.txt" (917 bytes), submitted via EFS-WEB and created on Sep. 15, 2010, is herein incorporated by reference.

FIELD OF THE INVENTION

The invention relates to peptides for use in reduction of cell proliferation and treatment of cancer, including metastatic cancer.

BACKGROUND OF THE INVENTION

A 54 amino acid paralytic peptide named soricidin (NCBI accession no. P0C2C6) was discovered and isolated from the submaxilary saliva gland of the Northern Short-tailed Shrew (*Blarina brevicauda*). A previous patent on the use of soricidin in treating pain (U.S. Pat. No. 7,119,168, incorporated by reference herein in its entirety) provided data that showed that this 54-mer peptide caused paralysis and inhibited calcium uptake by two ovarian cancer cell lines (U.S. Pat. No. 7,273,850, incorporated by reference herein in its entirety). There remains a need for anti-cancer agents that do not have paralytic activity.

One group of calcium ion channels implicated in cancer is the Transient Receptor Potential (TRP) channels that are found across the invertebrates and vertebrates. A member of the TRP super-family was named after it was discovered that activates in the presence of vanilloids (capsaicin from hot peppers for example) and are called Transient Receptor Potential Vanilloid. The first four of these receptors tested (TRPV1, TRPV2, TRPV3 and TRPV4) all responded to capsaicin and were also responsible for detecting changes in temperature. The remaining two of the TRPV sub-family, TRPV5 and TRPV6 were found predominantly in epithelial type tissues and were responsible for influx of calcium ion. TRPV5/6 were identified as responsible for import of calcium into epithelial tissues of the intestine and hence uptake of calcium from the diet. These channels were also shown to be present in a number of other tissues in varying amounts, but most notably intestinal epithelial cell, kidney, placenta and pancreas. The expression of TRPV6 was measured as highly elevated in human ovarian, prostate and mammary cancer, thyroid and colon tumors and in some known prostate cancer cell-lines. In prostate cancer, TRPV6 was hugely up-regulated in carcinomas that have breached to tissue wall and have begun to metastasize (Zhuang et al. 2002). TRPV6 is therefore a potential target for cancer therapy. Accordingly, there is a strong need for compounds that block the activity of the overabundant TRPV6 channels in cancer cells.

More recently, the involvement of TRPV6 in cancer has been suggested to activate a pro-survival/anti-apoptotic pathway in two cancer cell lines with over-expressed TRPV6. In the prostate cancer cell line (LnCaP) intracellular calcium concentrations, increased by greater levels of TRPV6, activate nuclear factor of activated T-cells (NFAT; Lehen'kyi et al. 2007). Bolanz et al. (2008) have also shown the involvement of calcium-activated NFAT in switching on anti-apoptotic genes in a human breast cancer cell line (T 47-D). Bolanz et al. showed that reducing the production of TRPV6 by interfering RNA seemed to relieve the apoptotic block. These reports further accentuate the need for TRPV6 inhibitors in cancer treatment.

SUMMARY OF THE INVENTION

The inventors have synthesized isolated peptides that provide calcium channel inhibition activity and, in particular, TRPV6 calcium channel inhibition activity. The peptides are useful for treating cancer, including metastatic cancer. Surprisingly, these compounds have sequence identity to a continuous string of amino acids in soricidin but they have calcium channel inhibition activity without paralytic activity. It was not previously known that the structure of soricidin that provided calcium channel inhibition activity was separate from the structure that caused paralytic activity. The peptides of the invention are optionally half the length of soricidin, or shorter. The peptides of the invention also unexpectedly have greater calcium channel inhibition activity than soricidin in some cells. It was also determined that the inhibition activity increased in some cells as peptide length decreased.

The peptides of the invention have other unexpected properties compared to full-length soricidin, such as increased solubility, increased shelf stability and reduced antigenicity. In one embodiment, the invention relates to an isolated peptide comprising all or part of the amino acid sequence: EGKLSSNDTE GGLCKEFLHP SKVDLPR (SEQ ID NO: 1), wherein the peptide inhibits calcium channel activity. The peptide is optionally KEFLHPSKVD LPR or HP SKVDLPR. Another aspect of the invention relates to method of inhibiting calcium uptake by a cancer cell, inducing cell apoptosis and/or preventing or treating cancer, comprising administering to the cell all or part of a peptide of the invention, wherein the peptide inhibits calcium uptake by the cancer cell. Optionally, the methods include administering all or part of a peptide of the invention and one or more chemotherapeutic agents such as a taxane-based agent, anthracycline-type agent or a platin-based agent. The cancer optionally comprises breast cancer, ovarian cancer, blood cancer, brain cancer, retinal cancer, liver cancer, thyroid cancer, colon cancer, prostate cancer, or endometrial cancer. The peptides of the invention inhibit calcium channel activity, such as TRPV6 calcium channel activity. The cancer optionally comprises a metastatic cancer, such as a metastatic cancer located in a lymph node, lung tissue, kidney tissue or liver tissue.

Another embodiment of the invention relates to a pharmaceutical composition comprising a peptide of the invention and a carrier. In one embodiment, there is provided a pharmaceutical composition comprising a peptide of the invention and one or more chemotherapeutic agents. In one embodiment, the chemotherapeutic agent comprises carboplatin and/or paclitaxel. The invention includes peptides of the invention for use in preparation of a medicament for inhibiting calcium channels in a cell, inducing apoptosis of a cancer cell and/or treatment of cancer. The invention also includes peptides of the invention for use in inhibiting calcium channels in a cell, inducing apoptosis of a cancer cell and/or treatment of cancer.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from the detailed description.

BRIEF DESCRIPTION OF THE DRAWINGS

Embodiments of the invention will be described in relation to the drawings in which:

FIG. 1 shows the net average change in calcium current ($I_{SOC}$) through TRPV6 channels as a function of peptide concentration (panel A). SorC13 is represented by open circles and broken line. SorC27 is represented by open squares and a solid line. Note that the positive numbers indicate inhibition (net current) of calcium current flowing into the cell. Panel B shows the percent of maximum inhibition of calcium current ($I_{SOC}$) through TRPV6 channels as a function of peptide concentration. SorC13 is represented by open circles and broken line. SorC27 is represented by open squares and a solid line.

FIG. 5 shows a comparison of the ratio of CAT treatment:CAT control (no CAT) to the ratio of SorC13 treatment:SorC13 control (no SorC13) and SorC27 treatment:SorC27 control (no SorC27) on SKOV3 (panel A). Panel B shows the comparison of CAT and SorC13 treatments on CaOV3. The concentration of SorC13 was 100 uM; SorC27 was 10 uM. CAT=Paclitaxel (10 uM) plus carboplatin (20 mM). The data points are the means of four measurements of induction of apoptosis. The dotted line is a 1:1 ratio obtained for no effect.

FIG. 10 shows the distribution of Cy5.5 labeled SorC27 in CD1 mice after i.v. injection over time after perfusion to wash out fluids. The Y-axis is the percentage of total fluorescence measured in all tissues. The highest percent uptake (of total fluorescence) of SorC27 was observed in liver, lung and kidney. Lymph node is not shown because perfusion washes out lymph. Panel A shows the distribution 4 hours after i.v. injection and Panel B 24 hours after i.v. injection.

FIG. 17 shows the anti-tumour activity of low, medium or high doses of Paclitaxel chemotherapy or low, medium or high doses of Paclitaxel chemotherapy and SorC13 expressed as a percentage change in tumour volume relative to the control (% ΔT/ΔC).

DETAILED DESCRIPTION OF THE INVENTION

Figure 2:
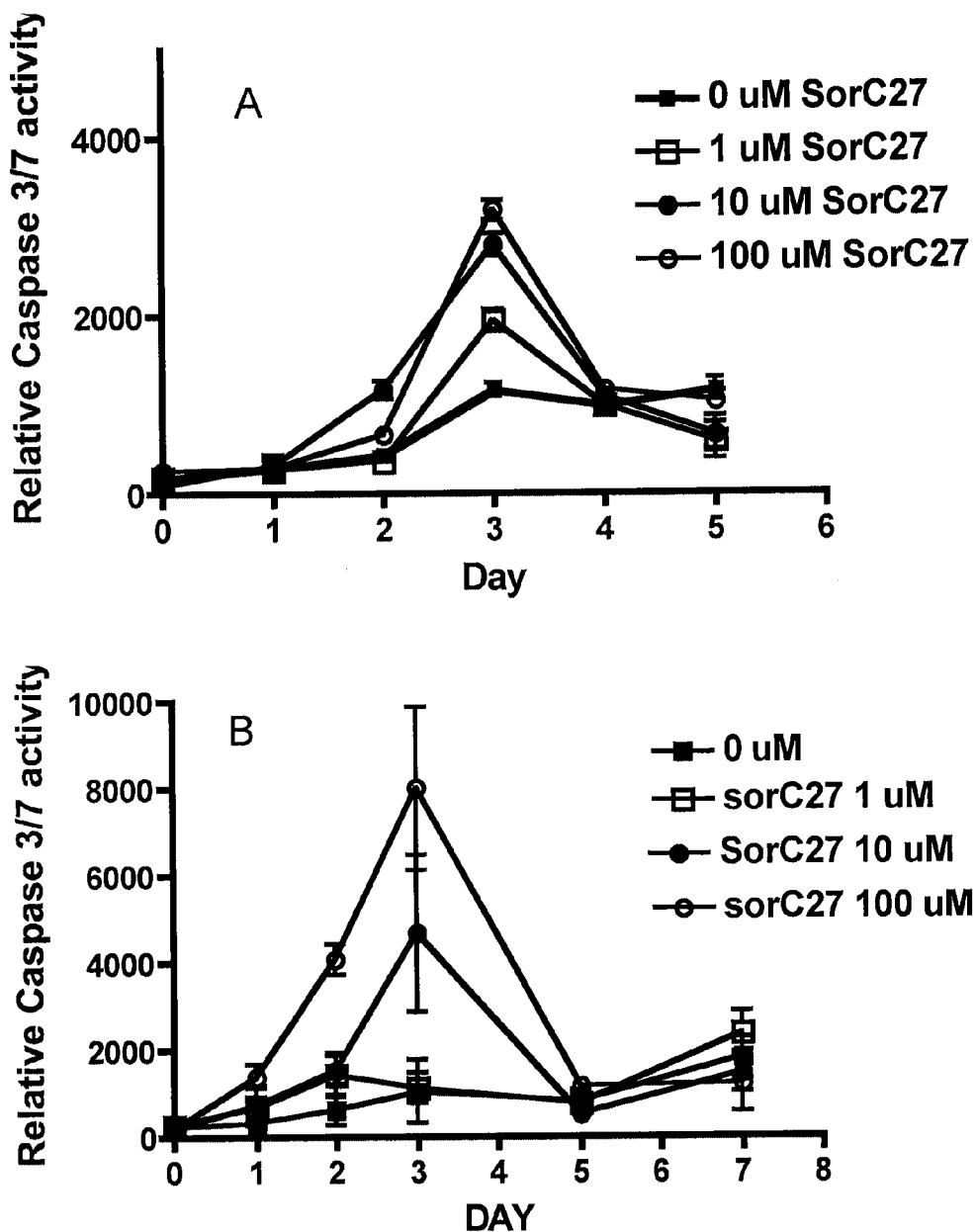
FIG. 2 shows the effect of SorC27 on an ovarian cancer cell line (SKOV-3, panel A) and a breast cancer cell line (MCF 7, panel B).

The inventors have made isolated peptides that provide calcium channel inhibition activity. In particular, the peptides have TRPV6 calcium channel inhibition activity and block TRPV6 function in cancer cells that have over-expressed TRPV6. The peptides are useful in methods of treating cancer, such as breast cancer, ovarian cancer, blood cancer (leukemia), brain cancer, retinal cancer, liver cancer, thyroid cancer, colon cancer, prostate cancer and endometrial cancer.

The peptides are also useful in methods of medical treatment of metastatic cancer that has originated in a first tissue and spread to a secondary site, such as a lymph node, liver, lung or kidney tissue.

In one embodiment, the peptide of the invention has the amino acid sequence: HPSKVDLPR (called "SorC9"; amino acid nos. 19-27 of SEQ ID NO:1). In another embodiment, the compound has the amino acid sequence KEFLHPSKVDLPR (called "SorC13"; amino acid nos. 15-27 of SEQ ID NO:1). In another embodiment, the compound comprises all or part of the amino acid sequence EGKLSSNDTEGGLCKEFLHPSKVDLPR (called "SorC27"; SEQ ID NO:1).

The invention also includes an isolated nucleic acid encoding a peptide of the invention, such as a nucleic acid encoding SEQ ID NO:1 or one of its fragments described herein. The invention also relates to isolated antibodies against a peptide of the invention. The antibody optionally selectively binds a peptide of the invention, but does not bind to soricidin.

Surprisingly, the compounds of the invention have sequence identity to part of soricidin but have calcium channel inhibition activity without paralytic activity. It was not previously known that soricidin had two functional domains in its structure. It was also unknown that peptides could be prepared that separated the calcium channel inhibition activity from the paralytic activity. The peptides of the invention are optionally half the length of soricidin, or shorter. The peptides of the invention not only isolate and retain calcium channel inhibition activity, they also unexpectedly have greater calcium channel inhibition activity than soricidin in certain cell lines, such as OV 2008. In certain cell lines, the inhibition activity also increased as peptide length decreased.

The surprising nature of this invention is emphasized by considering that, while bifunctionally large proteins and enzymes are common in biological systems, inherent bifunctionality is a very rare phenomenon in small peptides. Reports in the literature of bifunctionality have typically resulted from artificial production, for example, where two different peptides have been chemically fused (Anes et al. 2006; Yamamoto et al. 2008). The inventor determined that the N-terminal of soricidin has a paralytic function and the C-terminal has a calcium channel inhibitor function. Truncating soricidin at the N-terminal successfully produced peptides that retain calcium channel inhibition activity without paralytic activity.

The peptides of the invention have other unexpected properties compared to full-length soricidin. For example, the peptides of the invention have increased solubility, which allows smaller doses to be provided to achieve a target peptide concentration in blood plasma. Based on relative solubilities, the dose volume of the peptides of the invention to achieve a target blood concentration could be smaller than soricidin by at least 10-fold.

Additionally, the peptides have greater shelf-life stability and solution stability due to the presence of fewer sensitive disulfide bonds (soricidin has 3 disulfide bonds). The peptides of the invention optionally have no disulfide bonds. An absence of disulfide bonds provides a very long shelflife during storage under minimal refrigeration or at room temperature as a solid. Additionally when the peptides of the invention with no disulfide bonds are dissolved in water, cleavage of disulfide bonds cannot occur. Such cleavage, in full-length soricidin, can render the peptide less active and more susceptible to the formation of inter-molecular S—S bonds. The formation of inter-peptide S—S bonds also results in precipitation of soricidin. The peptides of the invention, such as SorC13 and SorC27, are typically stable in aqueous solution at 8° C. for at least 3 weeks with no change in purity as measured by HPLC.

The peptides of the invention also avoid one of the major adverse effects of pharmaceuticals, which is related to the ability to cross the central nervous system protective barrier, the blood-brain barrier. The inability of the peptides of the invention to cross this protective barrier obviates the potential toxicity in the central nervous system.

The peptides of the invention advantageously have low toxicity. As shown in Example 23, after in vivo i.v. injection into CD1 mice, SorC27 resulted in no change in blood pressure or heart rate over a 1 hour measurement period. There were no also neurological/behavioral changes over 72 hours. After in vivo i.v. injection into CD1 mice, SorC13 caused a small spike (approximately 25%) in blood pressure in the first 15 min which disappeared by 1 hour. There were no neurological/behavioral changes in the mice over 72 hours. Single intravenous injection of SorC13 or SorC27 into CD1 mice at doses of 10 mg/kg, 100 mg/kg and 500 mg/kg resulted in no adverse events over a 5-day post-injection observation period. Necropsy also showed no significant changes in all major organ systems. Furthermore, a multiple dose of SorC27 at 400 mg/kg (i.p.) each day for 12 days in mice showed no indication of toxicity.

The peptides of the invention, particularly the shorter peptides, such as SorC13, are typically less antigenic than soricidin. Peptides having a number of amino acids equal to or less than the empirical cutoff for antigenicity (typically considered to be 13 amino acids for peptides in general) possess no antigenicity.

As noted above, a peptide of the invention will have calcium channel activity (i.e. the ability to partially or totally inhibit channel activity) without paralytic activity. The peptides having such activity are readily identified with any known assays suitable for measuring i) calcium channel blocking and ii) lack of paralytic activity. For example, in one embodiment, a peptide having calcium channel inhibition activity is optionally identified by determining that the peptide reduces calcium channel activity by reducing (i.e., partially or fully inhibiting) the flow of calcium through calcium channels.

Figure 6:
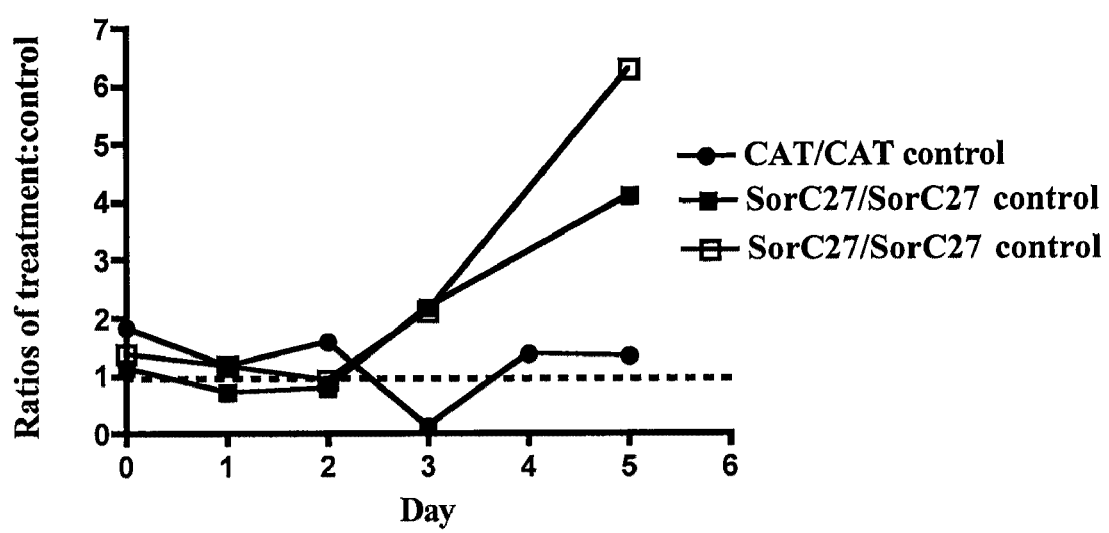
FIG. 6 shows a comparison of the ratio of CAT treatment:CAT control (no CAT) to the ratio of SorC27 treatment:SorC27 control (no SorC27) on OVCAR3. The concentrations of SorC27 were 10 uM (filled square) and 100 uM (empty square). CAT=Paclitaxel (10 uM) plus carboplatin (20 mM). The data points are the means of four measurements of induction of apoptosis. The dotted line is a 1:1 ratio obtained for no effect.

Calcium channel inhibition activity is optionally identified by a readily available cell line (e.g. human embryonic kidney cell lines-HEK, lymph node prostate cancer cell, LnCaP) transfected with an expression vector for TRPV6. Such transfected cells are readily aliquoted and stored (typically −80° C.) until required. This provides a standard transfected cell preparation to test for inhibition of calcium ion uptake by the cells. Analysis of the calcium movement into the cell lines to identify peptides of the invention that provide reduced calcium channel activity is optionally done by fluorometric measurement (internalized FURA calcium ion probe) or by an electrophysiological protocol involving patch clamping cells and measuring calcium current in the presence or absence of a peptide. Optionally the peptides have an equilibrium inhibition constant of less than: 1000 nM, 150 nM or 100 nM in a LnCaP cell model while not affecting the sciatic nerve transmission of an action potential in a rat sciatic nerve model (i.e., no paralytic activity). For example, the equilibrium dissociation constant (Kd) for SorC27 is 140 nM and SorC13 is 100 nM in the LnCaP model (FIG. 6). Based on a linear relationship with the number of amino acids, the Kd of SorC9 is expected to be approximately 90 nM.

The isolated peptides are useful for a number of purposes. In one embodiment, the invention includes methods of reducing cell proliferation by administering a peptide of the invention to a cell, such as a cancer cell. Reduction in cell proliferation is readily determined by contacting a peptide with a proliferating cell, such as a cancer cell, in vitro or in vivo, and determining whether the peptide reduces (i.e., fully or partially) inhibits cell proliferation. In another embodiment, the invention includes methods of inducing apoptosis of a cell, such as a cancer cell, by administering a peptide of the invention to the cell. Reduction in cell proliferation is readily determined by contacting a peptide with a cell, such as a cancer cell, in vitro or in vivo, and determining whether the peptide induces apoptosis.

As noted above, the isolated peptides are useful for treating cancer. The invention includes methods of treating cancer in a mammal, such as a human, by administering an isolated peptide of the invention to the mammal. Remarkably, in separate head-to-head tests against the well-known cancer drug, Paclitaxel, and the cancer drug cocktail, Paclitaxel and carboplatin ("CAT cocktail"), two peptides of the invention, SorC13 and SorC27, provided faster and more active induction of apoptosis in certain cell lines. This superior effect has been shown against both breast cancer and ovarian cancer. A typical treatment for breast cancer is Paclitaxel and a typical treatment for ovarian cancers is the CAT cocktail. In other cell lines, the performance of SorC13 and SorC27 was comparable to CAT.

The isolated peptide SorC27 has also been shown to be useful for treating cancer in an in vivo xenograft mouse cancer model. As shown in Example 14 and FIG. 12, in NOD/SCID mice xenografted with human ovarian cancer tumors SorC27 reduced the tumor volume significantly (p<0.05) when compared to the control situation (saline injection) and was not distinguishable from mice treated with CAT, over 12 days when tumor size was normalized to body weight.

Without wishing to be bound by theory on the cause of the anti-cancer effect, the inventor has determined, through experiments with SorC27 and SorC13, that the peptides of the invention activate the apoptosis cascade through caspase 3 and/or 7 in ten different cancer cells lines but not in two non-cancerous cell lines.

Therefore, a peptide of the invention is optionally identified as having anti-cancer activity if it causes induction of the enzymes caspase 3 and caspase 7 above the control cell levels of caspase 3 and caspase 7. Once these enzymes are activated, cell death will occur. The activity of the caspase enzymes in treated cells is readily measured and compared to control, untreated cells.

Furthermore, as shown in Table 9 and Example 25, the presence of TRPV6 mRNA in a cell line corresponds with those cell lines that exhibit an apoptotic effect in response to the peptides of the present invention.

In a further aspect of the invention, the peptides of the invention in combination with other chemotherapeutic agents have been shown to be effective in treating cancer using in vivo xenograft mouse cancer models. As used herein, "chemotherapeutic agent" refers to substance that reduces the proliferation of cancer cells, for example by prolonging the cancer cell cycle or killing cancer cells. Examples of chemotherapeutic agents include, but are not limited to, taxane-based drugs, platin-based drugs, anthracyclines (e.g. doxorubicin, cyclophosphamide), topoisomerase II inhibitors (e.g. etoposide), alkylating agents (e.g. ifosfamide) plant alkaloids (e.g. vinorelbine), and antimetabolites (e.g. fluorouracil).

As shown in Example 26, the use of SorC13 in combination with CAT (carboplatin and taxane (paclitaxel)) chemotherapy was highly effective in reducing the volume of human ovarian adenocarcinoma cell line SKOV3 xenograft tumours relative to a control. Furthermore, as shown in Example 27 and in FIGS. 16 and 17, the use of SorC13 in combination with Paclitaxel was also highly effective in reducing the volume of breast cancer T47D xenograft tumours relative to a control and also in shrinking tumour volume. Additionally, the effects of SorC13 in combination with Paclitaxel were shown to extend into a 12-day rest period post-treatment. The peptides described herein are therefore useful in combination with chemotherapeutic agents for the treatment of cancer. In one embodiment, administration of the peptides described herein can be used to reduce the amount of another chemotherapeutic agent that is necessary in order to reach a certain chemotherapeutic effect such as a reduction in tumour volume.

Metastatic Cancer

Figure 7:
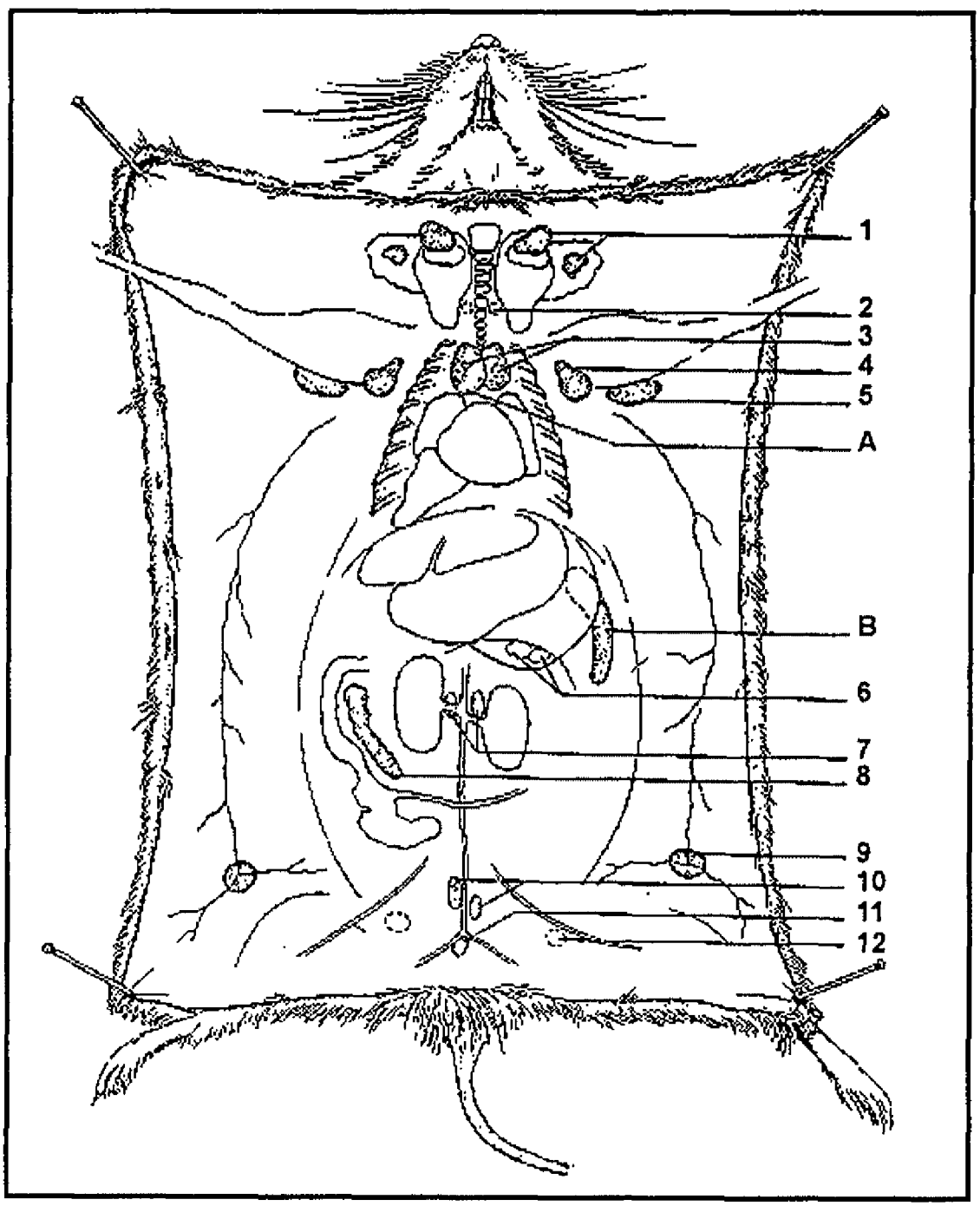
FIG. 7 is a line drawing showing the location of the lymph nodes in the mouse. Significant accumulation of SorC13-Cy5.5 and SorC27-Cy5.5 four hours after i.v. injection of 100 ug of each of the labeled peptides into CD1 mice was observed at the following lymph nodes labeled in FIG. 7: 1. Superfacial cervical nodes; 4. Axillary nodes; 5. Branchial nodes; 8. Mesenteric nodes; and 9. Inguinal nodes.

The peptides of the invention have anti-cancer activity against a cancer cell in a primary tumor site or a metastasized cancer cell in a secondary cancer site. The peptides localize predominantly in lymph nodes, but also in lung, liver and kidney, which are common sites where metastatic cancer is located (FIG. 7).

The peptides of the present application are useful in the treatment of metastatic cancer, including a cancer that has spread to the lung, brain, liver, kidney, spleen and bone marrow. The peptides can be used alone or in a pharmaceutical composition comprising a second anti-cancer agent.

The peptides of the present application are particularly useful in treating lymph node metastases. "Lymph node metastases" optionally include lung cancer (Mujoomdar et al, 2007), gastric cancer, cervical carcinoma (Lyshchik et al., 2007), vulvar carcinoma (Vernooij et al, 2007), endometrial cancer (Aalders et al, 2007), head and neck squamous cell carcinoma (Veness et al., 2007), esophagus and throat cancer, nasopharyngeal carcinoma (Ma et al., 2007), gastrointestinal cancer (Wind et al., 2006), Gall bladder cancer, brain cancer (Mujoomdar et al., 2007), thyroid cancer, breast cancer, ovarian cancer, prostate cancer and colorectal cancer. The peptides of the invention are therefore useful in treating cancer in a mammal at any of cancer stages I, II, III or IV.

Peptides of the Invention

Isolated peptides comprising all or part of any of SEQ ID NO:1 and having calcium channel inhibition activity (TRPV6 inhibition activity), without paralytic activity, are useful peptides for treatment of cancer. Amino acids may be added to the peptides of the invention. The isolated peptides, with amino acids, are typically 35 or 30 amino acids or less, optionally less than: 27, 25, 20, 15 or 13 amino acids long, while optionally at least 9 amino acids long. Typically the peptides are at least 9 contiguous amino acids of a sequence in this application, optionally 9-15, 16-27 or 28-35 amino acids. One can readily make longer peptides by adding a variety of additional amino acids to the SorC27 sequence to make a peptide that could be up to, for example, 30, 35, 40 or 45 amino acids long (e.g. additional amino acids corresponding to the soricidin amino acid sequence such as one or more of the C-terminal amino acids (SILARPAELNTETCILEC SEQ ID NO:2), a targeting sequence, or other amino acids).

The peptide optionally comprises, consists essentially of or consists of the amino acid sequence: HPSKVDLPR (amino acid nos. 19-27 of SEQ ID NO:1), KEFLHPSKVDLPR (amino acid nos. 15-27 of SEQ ID NO:1) or EGKLSSNDTEGGLCKEFLHPSKVDLPR (SEQ ID NO:1). Optionally the peptide comprises at least: 9, 10, 11, 12, 13, 14, 15, 16, 17, 18, 19 or 20 amino acids of SEQ ID NO:1. Optionally, the isolated peptide comprises at least: 9, 10, 11, 15 or 18 amino acids of SEQ ID NO:1. Optionally, the peptide comprises a fragment of 9-13, 10-15, 15-20, 20-25 or 20-27 amino acids of SEQ ID NO:1, wherein the peptide inhibits calcium channels, reduces cell proliferation and does not have paralytic activity.

The peptides of the invention optionally also include analogs of the aforementioned peptides. Analogs of the protein of the invention optionally include, but are not limited to an amino acid sequence containing one or more amino acid substitutions, insertions, deletions and/or mutations. Amino acid substitutions may be of a conserved or non-conserved nature. Conserved amino acid substitutions involve replacing one or more amino acids of the peptides of the invention with amino acids of similar charge, size, and/or hydrophobicity characteristics. When only conserved substitutions are made, the resulting analog should be functionally equivalent. Non-conserved substitutions involve replacing one or more amino acids of the amino acid sequence with one or more amino acids which possess dissimilar charge, size, and/or hydrophobicity characteristics. The analog is optionally a peptoid, which is an N-substituted polyglycine with amino acid R groups attached at the N atom.

One or more amino acid insertions are optionally introduced into the amino acid sequences of the invention. Amino acid insertions consist of single amino acid residues or sequential amino acids ranging for example from 2 to 15 amino acids in length.

Deletions consist of the removal of one or more amino acids, or discrete portions from the amino acid sequence of the peptide. The deleted amino acids may or may not be contiguous.

The peptides of the invention are readily prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart).

Analogs of a protein of the invention are optionally prepared by introducing mutations in a nucleotide sequence encoding the peptide. Mutations in nucleotide sequences constructed for expression of analogs of a protein of the invention preserve the reading frame of the coding sequences. Furthermore, the mutations will preferably not create complementary regions that could hybridize to produce secondary mRNA structures such as loops or hairpins, which could adversely affect translation of the mRNA.

Mutations are optionally introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures are employed to provide an altered gene having particular codons altered according to the substitution, deletion, or insertion required. Deletion or truncation of a peptide of the invention is also readily achieved by utilizing convenient restriction endonuclease sites adjacent to the desired deletion. Subsequent to restriction, overhangs may be filled in, and the DNA re-ligated. Exemplary methods of making the alterations set forth above are disclosed by Sambrook et al (Sambrook J et al. 2000. Molecular Cloning: A Laboratory Manual (Third Edition), Cold Spring Harbor Laboratory Press).

In addition, analogs of a protein of the invention are readily prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart). The peptides of the invention also include peptides having sequence identity to a peptide of the invention, mutated peptides and/or truncations thereof as described herein. Such peptides have amino acid sequences that correspond to nucleic acid sequences that hybridize under stringent hybridization conditions (see discussion of stringent hybridization conditions herein) with a probe used to obtain a peptide of the invention. Peptides having sequence identity will often have the regions which are characteristic of the protein.

Other useful peptides of the invention optionally comprise, consist essentially of or consist of an amino acid sequence with at least: 30%, 40%, 50%, 60%, 70%, 80%, 90% or 95% sequence identity to all or part of SEQ ID NO:1 described herein, wherein the peptide has calcium channel inhibition activity and no paralytic activity and is useful for treatment of cancer. Sequence identity is typically assessed by the BLAST version 2.1 program advanced search (parameters as above; Altschul, S. F., Gish, W., Miller, W., Myers, E. W. & Lipman, D. J. (1990) "Basic local alignment search tool." J. Mol. Biol. 215:403_410). BLAST is a series of programs that are available online through the U.S. National Center for Biotechnology Information (National Library of Medicine Building 38A Bethesda, Md. 20894) The advanced Blast search is set to default parameters. References for the Blast Programs include: Altschul, S. F., Gish, W., Miller, W., Myers, E. W. & Lipman, D. J. (1990) "Basic local alignment search tool." J. Mol. Biol. 215:403-410; Gish, W. & States, D. J. (1993) "Identification of protein coding regions by database similarity search." Nature Genet. 3:266-272; Madden, T. L., Tatusov, R. L. & Zhang, J. (1996) "Applications of network BLAST server" Meth. Enzymol. 266:131-141; Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402); Zhang, J. & Madden, T. L. (1997) "PowerBLAST: A new network BLAST application for interactive or automated sequence analysis and annotation." Genome Res. 7:649-656).

The present invention also includes a protein of the invention conjugated with a selected protein, or a selectable marker protein to produce fusion proteins.

Therapeutic Methods

The peptides of the invention, such as all or part of SEQ ID NO:1 described herein, are useful for reducing cell proliferation, inducing cell apoptosis and preventing or treating cancer by administration of the peptide to a human.

The phrase "reducing cell proliferation" as used herein refers to slowing the rate of proliferation of a cell as compared to the rate of proliferation of a cell in the absence of the substance.

The phrase "inducing cell apoptosis" as used herein refers to increasing the rate of apoptosis of cells as compared to the rate of apoptosis of cells in the absence of the substance.

The term "effective amount" as used herein means an amount effective and at dosages and for periods of time necessary to achieve the desired result (e.g. optionally blocking calcium channel activity, reducing cell proliferation, inducing apoptosis and/or preventing or treating cancer).

Administering a peptide or substance to a mammal includes both in vivo and ex vivo administrations.

The term "a cell" as used herein includes a single cell as well as a plurality or population of cells. Administering a peptide or substance to a cell includes both in vitro and in vivo administrations.

The phrase "reduce calcium channel activity" as used herein means that the substance can result in a decrease in calcium channel activity as compared to calcium channel activity in the absence of the substance.

The peptides of the invention strongly inhibit calcium uptake in cancer cells particularly cancer cells in which the calcium uptake channel TRPV6 has increased expression, such as in breast cancer, ovarian cancer, blood cancer, brain cancer, retinal cancer, liver cancer, thyroid cancer, colon cancer, prostate cancer and endometrial cancer. The peptides of the invention, by reducing calcium uptake, disrupt intracellular calcium essential for proliferation of normal and cancerous cells. Therefore, the invention includes the use of a peptide of the invention for reducing cell proliferation, inducing apoptosis and/or preventing or treating tumours and cancer in mammals (e.g. humans) by administration of the peptide to the mammal.

As used herein, and as well understood in the art, "to treat" or "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease or disorder, preventing spread of disease or disorder, delay or slowing of disease or disorder progression, amelioration or palliation of the disease or disorder state, and remission (whether partial or total), whether detectable or undetectable. "Treatment" can also mean prolonging survival as compared to expected survival if not receiving treatment.

Pharmaceutical Compositions

The invention also includes the use of the peptides of the invention for preparation of a medicament for treatment of cancer. The isolated peptides of the invention are optionally formulated into a pharmaceutical composition for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals.

Administration of a therapeutically active amount of pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of the substance to elicit a desired response in the individual. Dosage regimes may be adjusted to provide the optimum therapeutic response. For example, several divided doses may be administered daily or the dose may be proportionally reduced as indicated by the exigencies of the therapeutic situation.

The peptide of the invention is preferably combined with other components such as a carrier in a composition such as a pharmaceutical composition. The compositions are useful when administered in methods of medical treatment or prevention of cancer.

The pharmaceutical compositions can be administered to humans or animals by a variety of methods including, but not restricted to topical administration, oral administration, aerosol administration, intratracheal instillation, intraperitoneal injection, injection into the cerebrospinal fluid, intravenous injection and subcutaneous injection. Dosages to be administered depend on patient needs, on the desired effect and on the chosen route of administration. Nucleic acid molecules and peptides may be introduced into cells using in vivo delivery vehicles such as liposomes. They may also be introduced into these cells using physical techniques such as microinjection and electroporation or chemical methods such as co-precipitation, pegylation or using liposomes.

The pharmaceutical compositions are prepared by known methods for the preparation of pharmaceutically acceptable compositions which can be administered to patients, and such that an effective quantity of the nucleic acid molecule or peptide is combined in a mixture with a pharmaceutically acceptable vehicle. Suitable vehicles are described, for example in Remington's Pharmaceutical Sciences (Remington's Pharmaceutical Sciences, Mack Publishing Company, Easton, Pa., USA) or Handbook of Pharmaceutical Additives (compiled by Michael and Irene Ash, Gower Publishing Limited, Aldershot, England (1995). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456.

On this basis, the pharmaceutical compositions optionally includes an active compound or substance, such as a peptide or nucleic acid molecule, in association with one or more pharmaceutically acceptable vehicles or diluents, and contained in buffered solutions with a suitable pH and iso-osmotic with the physiological fluids. The methods of combining the active molecules with the vehicles or combining them with diluents are well known to those skilled in the art. The composition optionally includes a targeting agent for the transport of the active compound to specified sites within tissue. In one embodiment, the pharmaceutical compositions provided herein include one or more chemotherapeutic agents. In one embodiment, the chemotherapeutic agent is paclitaxel or carboplatin. In one embodiment, the pharmaceutical composition includes CAT (Carboplatin and Taxane). In one embodiment, the chemotherapeutic agent and the peptide are optionally separate compounds in a kit.

Preparation of Antibodies

Antibodies to the peptide are useful to identify the presence of the peptide in a test sample. Any method of labeling the antibody that would report on peptide density/location would be useful (e.g. radioactively labeled peptide or fluorescently tagged peptide). The antibody is typically a monoclonal antibody or a polyclonal antibody. The antibodies are also valuable for immuno-purification of peptides. For example, one may contact a biological sample with the antibody under conditions allowing the formation of an immunological complex between the antibody and a peptide recognized by the antibody and detecting the presence or absence of the immunological complex whereby the presence of the peptide of the invention is detected in the sample. The invention also includes compositions preferably including the antibody, a medium suitable for the formation of an immunological complex between the antibody and a peptide recognized by the antibody and a reagent capable of detecting the immunological complex to ascertain the presence of the peptides of the invention or similar peptides.

To recognize the peptides of the invention, one may generate antibodies against a range of unique epitopes throughout the peptides.

Monoclonal and polyclonal antibodies are prepared according to the description in this application and techniques known in the art. For examples of methods of the preparation and uses of monoclonal antibodies, see U.S. Pat. Nos. 5,688,681, 5,688,657, 5,683,693, 5,667,781, 5,665,356, 5,591,628, 5,510,241, 5,503,987, 5,501,988, 5,500,345 and 5,496,705 that are incorporated by reference in their entirety. Examples of the preparation and uses of polyclonal antibodies are disclosed in U.S. Pat. Nos. 5,512,282, 4,828,985, 5,225,331 and 5,124,147, which are incorporated by reference in their entirety.

The term "antibody" as used herein to include fragments thereof which also specifically react with a peptide of the invention. Antibodies can be fragmented using conventional techniques and the fragments screened for utility in the same manner as described above. For example, F(ab')2 fragments can be generated by treating antibody with pepsin. The resulting F(ab')2 fragment can be treated to reduce disulfide bridges to produce Fab' fragments.

The invention also includes methods of using the antibodies, such as in detection of receptors that bind to the peptides of the invention. For example, the invention includes a method for detecting the presence of a peptide of the invention by: a) contacting a sample containing one or more peptides with an antibody of the invention under conditions suitable for the binding of the antibody to peptides with which it is specifically reactive; b) separating unbound peptides from the antibody; and c) detecting antibody which remains bound to one or more of the peptides in the sample.

Research Tool

The peptides of the invention are useful in research protocols to explore the neuromuscular junction and ion channels. The ability to alter certain ion channels or classes of ion channels selectively provides another tool with which to perturb the neuromuscular-junction in a predictable manner. This identifies the role of susceptible peptide targets in neuromuscular functions and processes. The invention includes a method of determining the response of an ion channel to a paralytic peptide comprising contacting a channel or cells comprising a channel with a peptide of the invention or a derivative thereof and determining whether the channels transportions or whether ion transport (e.g. $Ca^{2+}$) has been reduced.

The peptides of the invention inhibit TRPV6 channels and are readily tagged with a label (fluorescent label, radioactive label, biotin label, etc.) to identify the TRPV6 channel in a cell or tissue, or to label cells or tissues that express large quantities of calcium channels. Accordingly, the invention relates to methods of identifying a TRPV6 channel in a cell or tissue, comprising contacting the cell or tissue with a peptide of the invention that has been tagged with detectable label and detecting the peptide bound to TRPV6 channel in the cell or tissue.

Nucleic Acids

The peptides of the invention (including truncations, analogs, etc.) may be prepared by chemical synthesis or by using recombinant DNA methods. Accordingly, the invention includes nucleic acid molecules having a sequence that encodes a peptide of the invention. These sequences are readily incorporated according to procedures known in the art into an appropriate expression vector that ensures good expression of the peptide. Expression vectors include but are not limited to cosmids, plasmids, or modified viruses (e.g., replication defective retroviruses, adenoviruses and adeno-associated viruses), so long as the vector is compatible with the host cell used. The expression "vectors suitable for transformation of a host cell", means that the expression vectors contain a nucleic acid molecule of the invention and regulatory sequences, selected on the basis of the host cells to be used for expression, which are operatively linked to the nucleic acid molecule. "Operatively linked" means that the nucleic acid is linked to regulatory sequences in a manner that allows expression of the nucleic acid.

The invention therefore includes a recombinant expression vector of the invention containing a nucleic acid molecule of the invention, or a fragment thereof, and the necessary regulatory sequences for the transcription and translation of the inserted peptide-sequence. Suitable regulatory sequences are optionally derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native compound and/or its flanking regions.

The invention further provides a recombinant expression vector comprising a DNA nucleic acid molecule of the invention cloned into the expression vector in an antisense orientation. These vectors are useful experimental systems to study the peptides of the invention or its variants or to test antidotes. The peptides may or may not be toxic to the host cells. They are also useful to produce large amounts of the peptide.

The recombinant expression vectors of the invention may also contain a selectable marker gene that facilitates the selection of host cells transformed or transfected with a recombinant molecule of the invention. Examples of selectable marker genes are genes encoding a protein such as G418 and hygromycin which confer resistance to certain drugs, beta-galactosidase, chloramphenicol acetyltransferase, or firefly luciferase. Transcription of the selectable marker gene is monitored by changes in the concentration of the selectable marker protein such as beta-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein.

Recombinant expression vectors can be introduced into host cells to produce a transformed host cell. These cells are useful experimental systems. Accordingly, the invention includes a host cell comprising a recombinant expression vector of the invention. The term "transformed host cell" is intended to include prokaryotic and eukaryotic cells which have been transformed or transfected with a recombinant expression vector of the invention. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual (Third Edition), Cold Spring Harbor Laboratory Press), and other such laboratory textbooks.

Suitable host cells include a wide variety of prokaryotic and eukaryotic host cells. For example, the peptides of the invention may be expressed in bacterial cells such as *E. coli, Pseudomonas, Bacillus subtillus*, insect cells (using baculovirus), yeast cells or mammalian cells. Other suitable host cells can be found in Goeddel, Gene Expression Technology: Methods in Enzymology 185, Academic Press, San Diego, Calif. (1991).

As an example, to produce peptides recombinantly, for example, E. coli can be used using the T7 RNA polymerase/promoter system using two plasmids or by labeling of plasmid-encoded proteins, or by expression by infection with M13 Phage mGPI-2. E. coli vectors can also be used with Phage lambda regulatory sequences, by fusion protein vectors (e.g. lacZ and trpE), by maltose-binding protein fusions, and by glutathione-S-transferase fusion proteins.

Alternatively, a peptide can be expressed in insect cells using baculoviral vectors, or in mammalian cells using vaccinia virus. For expression in mammalian cells, the cDNA sequence may be ligated to heterologous promoters and introduced into cells, such as COS cells to achieve transient or long-term expression. The stable integration of the chimeric gene construct may be maintained in mammalian cells by biochemical selection, such as neomycin and mycophoenolic acid.

The DNA sequence can be altered using procedures such as restriction enzyme digestion, fill-in with DNA polymerase, deletion by exonuclease, extension by terminal deoxynucleotide transferase, ligation of synthetic or cloned DNA sequences, site-directed sequence alteration with the use of specific oligonucleotides together with PCR. For example, one to five or five to ten amino acids or more may be removed or mutated.

The DNA sequence or portions thereof, or a mini gene consisting of a DNA with an intron and its own promoter, is introduced into eukaryotic expression vectors by conventional techniques. These vectors permit the transcription of the DNA in eukaryotic cells by providing regulatory sequences that initiate and enhance the transcription of the DNA and ensure its proper splicing and polyadenylation. The endogenous gene promoter can also be used. Different promoters within vectors have different activities that alter the level of expression of the cDNA. In addition, certain promoters can also modulate function such as the glucocorticoid-responsive promoter from the mouse mammary tumor virus.

Some of the vectors listed contain selectable markers or neo bacterial genes that permit isolation of cells by chemical selection. Stable long-term vectors can be maintained in cells as episomal, freely replicating entities by using regulatory elements of viruses. Cell lines can also be produced which have integrated the vector into the genomic DNA. In this manner, the gene product is produced on a continuous basis.

Vectors are introduced into recipient cells by various methods including calcium phosphate, strontium phosphate, electroporation, lipofection, DEAE dextran, microinjection, or by protoplast fusion. Alternatively, the cDNA can be introduced by infection using viral vectors.

Peptides of the invention are readily isolated from cells or tissues, including mammalian cells or tissues, in which the peptide is expressed.

The peptide is readily purified by conventional purification methods known to those in the art, such as chromatography methods, high performance liquid chromatography methods or precipitation.

For example, an anti-peptide antibody (as described herein) is readily used to isolate a peptide, which is then purified by standard methods.

The isolated peptides of the invention are also readily prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart).

EXAMPLES

The following examples illustrate embodiments of the invention and do not limit the scope of the invention.

Example 1

Separation of the Calcium Channel-Inhibitor Amino Acid Sequence from Soricidin

Sequences of amino acids from the carboxyl-terminal region of soricidin were synthesized. These segments have been named SorC13 (which has sequence identity to 13 amino acids at the C-terminal end of soridicin) and SorC27 (which has sequence identity to 27 amino acid sequence at the C-terminal end of soricidin). The amino acid sequences of SorC13 and SorC27 as well as some of their physical and physiological properties as are outlined in Table 1. The half-lives of SorC13 and SorC27 (as shown in Example 22) were lower than the half-life of Sor54.

TABLE 1

Summary Comparison of SorC54, SorC27 and SorC13

| Property | Sor54 | SorC27 | SorC13 |
|---|---|---|---|
| No. of amino acids | 54-mer | 27-mer | 13-mer |
| Molecular weight | 5806 (3 disulfide bonds) | 2957 (no disulfide bonds) | 1566 (no disulfide bonds) |
| Sequence | NCBI accession no. P0C2C6 | EGKLSSNDTEGGLCKEF LHPSKVDLPR (SEQ ID NO: 1) | KIEFLHPSKVDLPR |
| pI | 4.3 (measured) | ~5.6 (calculated) | ~8.3 (calculated) |
| Physical appearance | White solid | White solid | White solid |
| Solubility (aqueous) | <20 mg/mL | >200 mg/mL | >200 mg/mL |
| Purity | ≧95% | ≧95% | ≧95% |
| Stability in aqueous solution @−20° C. | stable | Very stable | Very stable |
| Stability solid @ −20° C. | stable | Very stable | Very stable |
| Stability solid @ Room Temp. | unstable | Very stable | Very stable |

TABLE 1-continued

Summary Comparison of SorC54, SorC27 and SorC13

| Property | Sor54 | SorC27 | SorC13 |
|---|---|---|---|
| Detection limit via direct HPLC | ≃ 200 ng | ≃ 200 ng | ≃ 200 ng |
| Physiology |  |  |  |
| Clearance route in iv mice @ 5 mg/kg | To be determined. | Rapid via kidney. | Rapid via kidney. |
| Cellular Target | voltage-gated sodium channels and TRPV6 | TRPV6 | TRPV6 |
| Physiol. effects in vivo (mealworm larvae); 5 mg/kg | Paralytic | Not paralytic | Not paralytic |
| Physiol. effects in vivo (mice) @ 5 mg/kg | Not tested. | None observed over 72 hr | 15% BP spike, @ 15 min, stabilizes by 1 hr, no observed effects up to 72 hrs |
| Half-life in rat plasma | >30 hour; binds to plasma proteins | 21 min; doesn't bind to plasma proteins | 58 min; doesn't bind to plasma proteins |
| Half-life in human plasma | >30 hours; binds to plasma proteins | 20 min; doesn't bind to plasma proteins | 56.6 min; doesn't bind to plasma proteins |
| Maximum Tolerated Dose in CD-1 mice by single i.v. dose 10, 100 and 500 mg/kg doses | Not tested | No toxic effects | No toxic effects |
| Repeated dose in NOD/SCID mice @ 400 mg/kg, daily i.p. injection for 12 days | Not tested | No loss of body weight compared to controls, no toxic effects noted | No loss of body weight compared to controls, no toxic effects noted |

"Very stable" in the above table means that there was no observable degradation of the solid peptides over 6 months. As a solution in sterile water, the peptides are typically stable for at least 3 weeks at 8° C. and at −20° C., are expected to be stable more than 1 year.

SorC27 and SorC13 do not exhibit paralytic activity. To show this, the mealworm larva paralytic bioassay reported previously (U.S. Pat. No. 7,119,168) was used. Animals from a mealworm colony were arbitrarily selected and placed in groups (treatment and control). The animals were weighed to allow calculation of equivalent doses. The treatment was with either SorC13 or SorC27 dissolved in buffered insect Ringer's solution. The control was injection was an equivalent volume of insect Ringer's (NaCl; 10.40 g; KCl, 0.32 g; $CaCl_2$, 0.48 g; $NaHCO_3$, 0.32 g dissolved in 1 L of Millipore sterile water, pH 7.4). Peptide formulations were: SorC27 solutions, prepared at 1.0 mg/100 uL insect Ringer's (10 ug/uL, 3.4 uM, MW=2957); and SorC13, prepared at 0.5 mg/100 uL (5 ug/uL, 3.4 uM, MW=1566). The doses were 50 ug SorC27 per 100 mg of animal mass and 25 ug SorC13 per 100 mg of animal mass. Peptide solutions and control saline were injected dorsally at the fourth segment from the head, just under the integumen. Animals were gently 'tail tweaked' with forceps to trigger the escape reflex reaction and scored on time-to-effect, duration of effect and intensity of effect. None of the animals treated with SorC13 or SorC27 exhibited any noticeable effects, while those animals treated with soricidin exhibited profound paralysis.

Table 2 shows the comparison of the number of larvae paralyzed by injection of the C-peptides compared to soricidin and to control saline injection. The shrew peptide (soricidin) is profoundly paralytic in the mealworm larva model. When the SorC27 and SorC13 peptides were injected into larvae at molar equivalent doses (20 nanomole/100 mg larva) there was no evidence of paralysis.

TABLE 2

Comparison of the activity of paralytic shrew soricidin with SorC13 and SorC27 derived from it. Animals were dosed at 20 nmole/100 mg mass.

| Time (min) | Control (saline) | Soricidin | SorC13 | SorC27 |
|---|---|---|---|---|
| 0 | 0/4 | 4/4 | 0/4 | 0/4 |
| 2 | 0/4 | 4/4 | 0/4 | 0/4 |
| 30 | 0/4 | 4/4 | 0/4 | 0/4 |

Example 2

SorC13 and Sor C27 Strongly Inhibit Calcium Ion Uptake Through the Transient Receptor Potential (Vallinoid) Six (TRPV6)

An expression vector (pCAGS-IRES-hTRPV6b) (Bodding et al. 2003) containing the nucleotide code for human TRPV6b was transfected into and expressed by human lymph node prostate cancer (LnCaP, ATCC CRL-1740). Patch clamping with whole-cell current acquisition was used to measure the calcium current through this channel. Cells were treated and calcium store operated current ($I_{SOC}$) was measured with either SorC13 (n=90) or SorC27 (n=30) in a closed-circuit perfusion for 3 min at each of cumulative concentrations of 0 (baseline), 100 nM, 500 nM 1 uM, 30 uM and 100 uM. Washout perfusion was done at 2 mL/min for 3 min. The positive control used was a known store operated channel (SOC) inhibitor MRS-1845 (N-propargylnitrendipene; available from Sigma Aldrich) at 5 uM and, in this system, demonstrated inhibition of the calcium current. A summary of the effects of SorC13 and SorC27 are shown in FIG. 1. It is clear that both of the C-peptides strongly inhibited the flow of calcium through the TRPV6 channel. Fitting the data to a hyperbolic function allowed calculation of the concentration providing 50% inhibition of the SOC, for SorC13 ($I_{SOC-50}$=0.10 uM) and SorC27 ($I_{SOC-50}$=0.14 uM). Further, both C-peptides are very strong inhibitors of calcium current through the TRPV6 channel with inhibition constants in the 100 nM range.

Example 3

SorC13 and SorC27 Induce Apoptosis in Human Breast and Ovarian Cancer Cell Lines, Particularly Trpv6 Cancer Cell Lines The peptides of the invention are useful for inducing apoptosis in cells in vitro and in vivo, particularly in cancer cells such as the cell lines listed in Table 3. The cell lines used to model human breast cancer and human ovarian cancer were obtained from the American Type Culture Collection (ATCC) and grown under the recommended conditions and in culture media recommended by ATCC.

Culture of Cancer Cell Lines

The cell lines were cultured under sterile conditions at 37° C., in a humidified 5% $CO_2$ atmosphere. Culture media used are listed below for each cell line:

T 47D was cultured in RPMI medium (Sigma-Aldrich) modified with 15% fetal bovine serum, 2 mM L-glutamine, 1 mM sodium pyruvate, 0.1 mg/mL bovine insulin and penicillin plus streptomycin mixture (50 ug/mL each).

MCF-7, MDA-MB-231, MDA-MB-415, MDA-MB-468 were grown in DMEM modified with 10% (v/v) fetal bovine serum, 2 mM L-glutamine and 50 ug/mL each of penicillin and streptomycin.

MCF-10A, MCF-12A were cultured in 50% DMEM plus 50% Ham's F12 modified with 2 mM L-glutamine, 1 mM sodium pyruvate, 0.01 mg/mL bovine insulin, 500 ng/mL hydrocortisone, 50 ug/mL of penicillin and streptomycin. The combined medium was supplemented with 5% (v/v) fetal bovine serum.

OVCAR-3 was cultured in RPMI 1640 medium supplemented with 1.0 mM sodium pyruvate, 0.01 mg/mL insulin and 10% (v/v) fetal bovine serum.

SKOV-3 was cultured in McCoy's % A medium supplemented with 1.5 mM L-glutamine, 2.2 g/L sodium bicarbonate and 10% (v/v) fetal bovine serum.

CAOV-3 was cultured in Dulbecco's Modified Eagle Medium (4.5 g/L glucose) with 4 mM L-glutamine, 1.5 g/L sodium bicarbonate and 10% (v/v) fetal bovine serum.

OV-90 was cultured in a 1:1 mixture of MCDB 105 medium and Medium 199 supplemented with 15% (v/v) fetal bovine serum.

HeyC2 was cultured in RPMI 1640 medium supplemented with 1.0 mM sodium pyruvate, 0.01 mg/mL insulin and 10% (v/v) fetal bovine serum.

TABLE 3

List of human breast and ovarian cancer cell lines tested for the induction of apoptosis by SorC13 and/or SorC27

| Cell Line | ATCC number | Description |
|---|---|---|
| Human Breast Cancer Lines | | |
| MCF 7 | HTB-22 | Non-invasive mammary gland epithelial adenocarcinoma |
| MDA-MB-231 | HTB-26 | Invasive mammary epithelial adenocarcinoma |
| MDA-MB-415 | HTB-128 | Human mammary gland adenocarcinoma |
| MDA-MB-468 | HTB-132 | Human mammary gland adenocarcinoma |
| T 47D | HTP-133 | Human mammary gland ductal carcinoma |
| Human Breast Non-Cancer Cell Lines | | |
| MCF-10A | CRL-10317 | non-tumorigenic mammary gland epithelial |
| MCF-12A | CRL-10782 | Human mammary gland epithelial, spontaneous immortalization |
| Human Ovarian Cancer Cell Lines | | |
| CaOV-3 | HTB-75 | Human ovarian adenocarcinoma |
| OVCAR-3 | HTB-161 | Human ovary epithelial adenocarcinoma |
| OV-90 | CRL-11732 | Human ovarian malignant papillary serous adenocarcinoma |
| SKOV-3 | HTB-77 | Human ovarian adenocarcinoma |
| HEY C-2 | | Human ovarian epithelial cancer |

MCF-7, MDA-MB-468, MCF-10A, MCF-12A and OVCAR-3 were tested for the induction of apoptosis by both SorC13 and SorC27. T 47D and CaOV-3 were tested for the induction of apoptosis by SorC13. MDA-MB-231 and MDA-MB-415 were tested for the induction of apoptosis by SorC27. The other cell lines were tested with SorC13 and SorC27 using a similar methodology to show that the C-peptides induce apoptosis.

Monitoring Induction of Apoptosis and Cell Viability

The levels of apoptotic induction and cell viability were determined by multiplexing the measurements for single samples. CellTiter Blue and APO-ONE assay systems from Promega allows the determination of cell viability correlated to cell number, and induction of apoptosis. This protocol uses a fluorgenic peptide that contains a peptide recognition-sequence for caspase 3 and caspase 7, initiating proteolytic enzymes of the apoptosis cascade. The CellTiter Blue reagent was added to wells in a 96-well plate containing cells under test, immediately after addition of peptide solution or vehicle. About 5000 cells were plated into the wells the day before. At the chosen time (Day 1, Day 2 etc.) the fluorescence was measured at 590 nm (emission) after excitation at 560 nm. The caspase 3/7 activity was measured (485 nm Ex/527 nm Em) in the same wells after adding 120 uL of the Apo-ONE reagent, freeze fracturing at −80° C. for 1 hr, and incubating for 1 hr at room temperature.

For this work, the concentrations of SorC13 and SorC27 used were 0 uM, 1 uM, 10 uM and 100 uM. The experiments extended over a 5 to 7 day period. All measurements were done in quadruplicate with both a blank (no cells) and control (vehicle, no peptide) used to correct the test measurements. The time-response data, and the dose-response data were plotted as means±standard error of the mean. Any statistical comparisons were done with the Student's t-test or by ANOVA analysis over the dose course. The level of statistical significance was considered to be the 95% confidence interval (i.e., $p \leq 0.05$).

Figure 3:
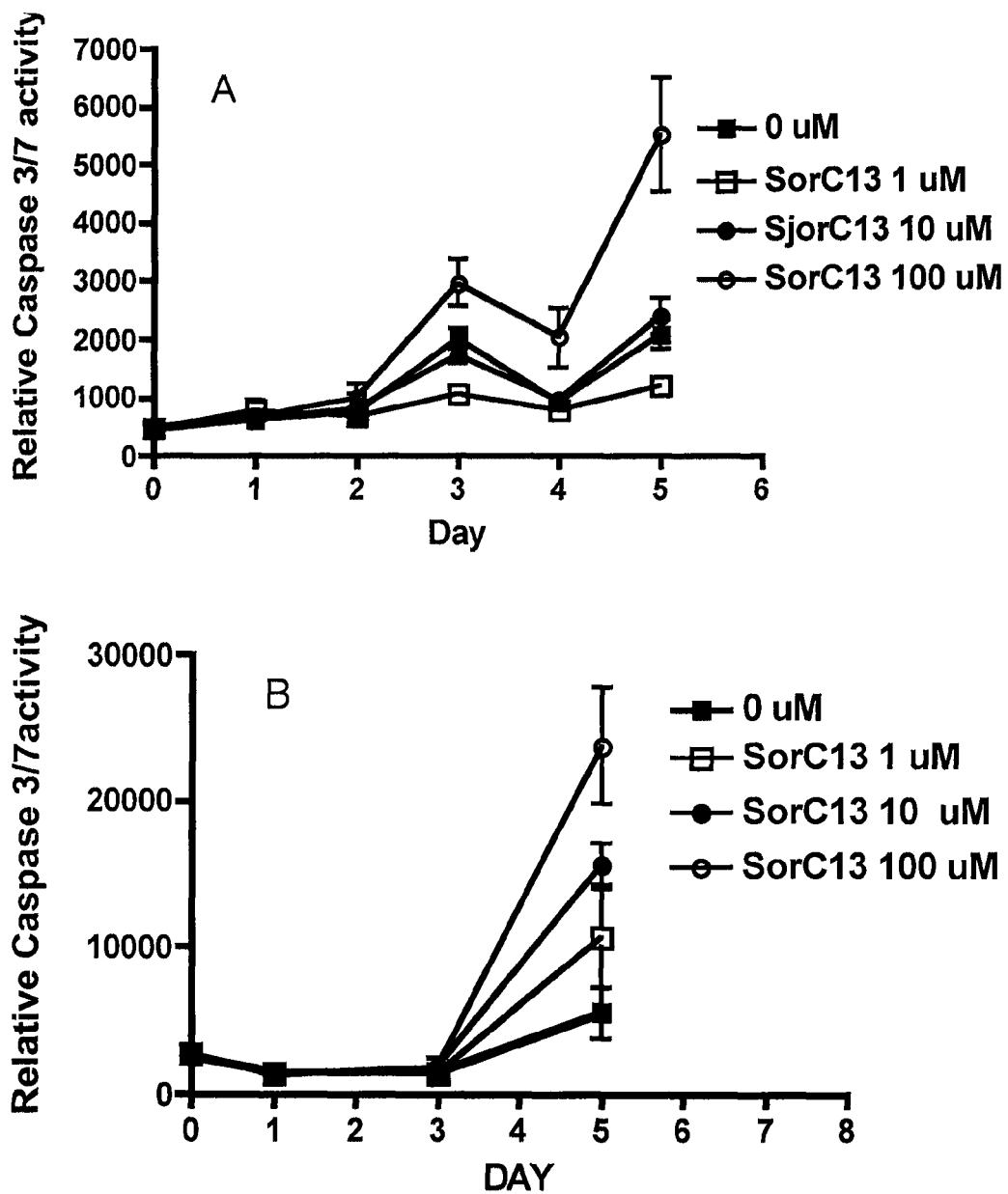
FIG. 3 shows the effect of SorC13 on an ovarian cancer cell line (SKOV-3, panel A) and a breast cancer cell line (T 47D, panel B).

Induction of apoptosis and attendant decrease was observed in cell viability in both breast and ovarian cancer cell lines. The effects of SorC27 on an ovarian (SKOV-3) and breast (MCF 7) cancer cell line are shown in FIG. 2. Similarly, the effect of SorC13 on ovarian and breast cancer cell lines is shown in FIG. 3. From the large increases in the activities of the caspase3/7 activity, it is clear that there is a time dependent effect and a dose dependent effect on the induction of apoptosis.

The observations of the effects of SorC13 on breast cancer cell lines are summarized in Table 4 and show:
  SorC13 induced apoptosis and decreased cell viability in three out of four cancerous cell lines at statistically significant levels.
  SorC13 induced apoptosis in T 47D (Table 4, FIG. 3B) at a statistically significant level.
  SorC13 did not induce apoptosis in two controls, non-cancerous cell lines (MCA 10A and MCA 12A).

The observations of the effects of SorC13 on ovarian cancer cell lines are summarized in Table 5 and show:
  3 ovarian cancer cell lines treated showed induction of the apoptotic cascade significantly above the 'no treatment' control (positive: CaOV3, OVCAR3, SKOV3).

The observations of the effects of SorC27 on breast cancer cell lines are summarized in Table 6 and show:
  4 cancerous breast cancer cell lines treated with SorC27 showed a significant apoptotic response in response to exposure to SorC27 (positive: MB 416, MB 468, MB 231, MCF 7).
  Non-cancerous breast cell lines (MCA 10A and MCA 12A) were not affected by SorC27.

The observations of the effects of SorC27 on ovarian cancer cell lines are summarized in Table 7 and show:
  4 ovarian cancer cell lines (0V90, OVCAR3, SKOV3, HEYC2) showed induction of apoptosis after treatment with SorC27. The effects ranged from 1.9-fold to 6.3-fold greater than control condition of no treatment.

TABLE 4

The effect of SorC13 on induction of apoptosis in human breast cancer cell lines. The table shows an Apoptotic Index (treatment response/control response; AI = 1 when there is no effect). Also shown is an indication of whether cell viability decreased (+) or not (−). Two non-cancerous breast cell lines are included for comparison (MCF 10A and 12A).

| Breast cancer cell line | Concentration of SorC13 (uM) | Apoptosis Index (1 = no effect) | Statistical significance | Decline in cell viability |
|---|---|---|---|---|
| MB 468 | 1 | 2.7 | $p < 0.05$ | + |
|  | 10 | 3.3 | $p < 0.05$ | + |
|  | 100 | 2.7 | $p < 0.05$ | + |
| T 47D | 1 | 2.0 | $p < 0.05$ | + |
|  | 10 | 2.8 | $p < 0.05$ | + |
|  | 100 | 4.3 | $p < 0.05$ | + |
| MCF 7 | 1 | 1.2 | $p > 0.05$ | − |
|  | 10 | 1.1 | $p > 0.05$ | − |
|  | 100 | 2.4 | $p < 0.001$ | + |
| MCF 10A | 100 | 1.0 | — | − |
| MCF 12A | 100 | 1.0 | — | − |

TABLE 5

The effect of SorC13 on induction of apoptosis in human ovarian cancer cell lines. The table shows an Apoptotic Index (treatment response/control response; AI = 1 when there is no effect). Also shown is an indication of whether cell viability decreased (+) or not (−).

| Ovarian cancer cell line | Concentration of SorC13 (uM) | Apoptosis Index (1 = no effect) | Statistical significance | Decline in cell viability |
|---|---|---|---|---|
| CaOV3 |  |  |  |  |
| Day5 | 100 | 2.7 | $p < 0.05$ | + |
| OVCAR3 |  |  |  |  |
| Day 4 | 100 | 1.4 | $p > 0.05$ |  |
| Day 5 | 100 | 1.7 | $p < 0.05$ | + |
| SKOV3 |  |  |  |  |
| Day 4 | 100 | 2.2 | $p > 0.05$ |  |
| Day 5 | 100 | 2.7 | $p < 0.05$ | + |

TABLE 6

The effect of SorC27 on a number of human breast cancer cell lines. The table shows an Apoptotic Index (treatment response/control response; AI = 1 when there is no effect). Also shown is an indication of whether cell viability decreased (+) or not (−). Two non-cancerous breast cell lines are included for comparison (MCF 10A and 12A).

| Breast Adenocarcinoma cell line | Concentration of SorC27 (μM) | Apoptosis Index (1 = no effect) | Statistical significance | Decline in cell viability |
|---|---|---|---|---|
| MB 231 |  |  |  | + |
| Day 3 | 10 | 1.5 | $p < 0.05$ |  |
|  | 100 | 1.7 | $p < 0.01$ |  |
| MCF 7 |  |  |  | + |
| Day 2 | 10 | 1.0 | $p > 0.05$ |  |
|  | 100 | 2.8 | $p < 0.001$ |  |
| Day 3 | 10 | 2.9 | $p < 0.05$ |  |
|  | 100 | 4.6 | $p < 0.001$ |  |
| MB 415 | 10 | 1.3 | $p < 0.05$ | + |
|  | 100 | 1.5 | $p < 0.01$ |  |
| MB 468 |  |  |  | + |
| Day 3 | 10 | 1.1 | $p = 0.07$ |  |
|  | 100 | 1.2 | $p < 0.01$ |  |
| MCF 10A | 100 | 1.0 | — | − |
| MCF 12A | 100 | 1.0 | — | − |

TABLE 7

The effect of SorC27 on a number of human ovarian cancer cell lines. The table shows an Apoptotic Index (treatment response/control response; AI = 1 when there is no effect). Also shown is an indication of whether cell viability decreased (+) or not (−).

| Ovarian cancer cell line | Concentration SorC27 of (uM) | Apoptosis Index (1 = no effect) | Statistical significance | Decline in cell viability |
|---|---|---|---|---|
| HEY C2 |  |  |  | + |
| Day 6 | 100 uM | 1.4 | $p < 0.05$ |  |
| Day 7 | 10 uM | 2.2 | $p < 0.05$ |  |
|  | 100 uM | 2.8 | $p < 0.05$ |  |
| OV90 |  |  |  | + |
| Day 2 | 100 uM | 1.8 | $p = 0.003$ |  |
| Day 3 | 1 uM | 1.2 | $p = 0.026$ |  |
|  | 10 uM | 1.9 | $p = 0.001$ |  |
|  | 100 uM | 1.9 | $p = 0.001$ |  |
| OVCAR3 |  |  |  | + |
| Day 3 | 10 uM | 2.2 | $p = 0.0026$ |  |
|  | 100 uM | 2.2 | $p = 0.003$ |  |
| Day 5 | 10 uM | 4.1 | $p < 0.0001$ |  |
|  | 100 uM | 6.3 | $p < 0.0001$ |  |

TABLE 7-continued

The effect of SorC27 on a number of human ovarian cancer cell lines. The table shows an Apoptotic Index (treatment response/control response; AI = 1 when there is no effect). Also shown is an indication of whether cell viability decreased (+) or not (−).

| Ovarian cancer cell line | Concentration SorC27 of (uM) | Apoptosis Index (1 = no effect) | Statistical significance | Decline in cell viability |
|---|---|---|---|---|
| SKOV3 | | | | + |
| Day 2 | 10 uM | 2.7 | p = 0.0008 | |
| | 100 uM | 1.5 | p = 0.09 | |
| Day 3 | 1 uM | 1.7 | p = 0.0012 | |
| | 10 uM | 2.4 | p < 0.0001 | |
| | 100 uM | 2.7 | p < 0.0001 | |

Example 4

Analysis of SorC13 and SorC27 Against Paclitaxel in the Induction of Apoptosis in Metastatic Human Breast Cancer Cell Lines To benchmark the effect of both C-type peptides to the gold-standard treatment presently used against breast cancer (Paclitaxel), SorC13, SorC27 and Paclitaxel (10 uM) were compared. Both the APO-ONE assay (Promega) and the Cell-Titer Blue were used on the panel of breast cancer cell lines. The data were compared directly in terms of mean response and tested for significant difference.

The cell lines used were T47D and MCF7 and were obtained from the American Type Culture Collection (ATCC) and grown under the recommended conditions and in culture media recommended by ATCC. The cell lines were cultured under sterile conditions at 37° C., in a humidified 5% $CO_2$ atmosphere, using culture media as noted above.

Figure 4:
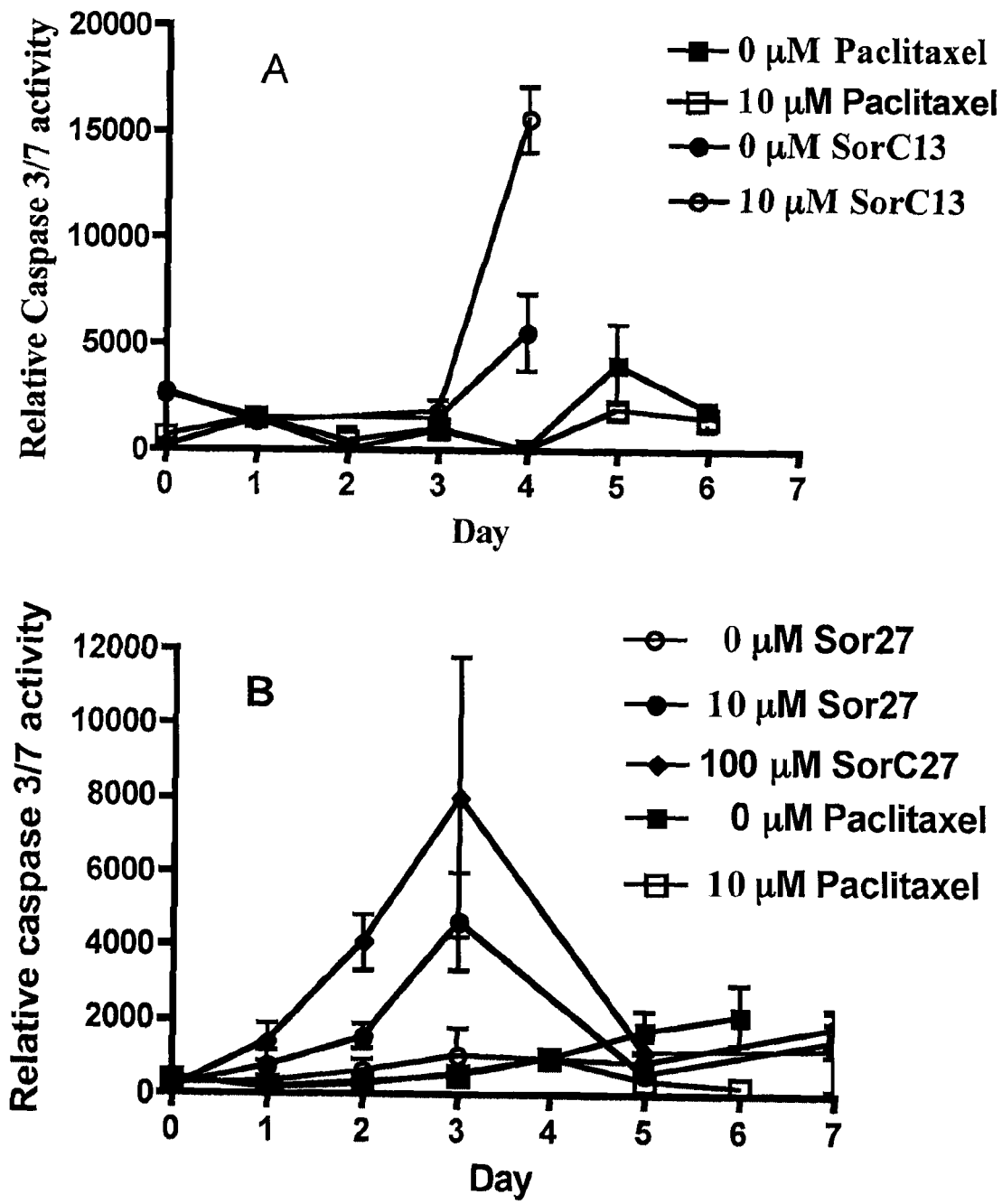
FIG. 4 shows a comparison of the induction of apoptosis by Paclitaxel (10 uM) and SorC13 (10 uM) in T 47D (panel A). Panel B shows a comparison of Paclitaxel (10 uM) and SorC27 (10 uM) in MCF 7.

The SorC-peptides had a profound effect when compared to Paclitaxel. As illustrated in FIG. 4, SorC13 was, in all cases, more effective at inducing a faster and more intense apoptotic response and, by this standard, more effective than Paclitaxel. SorC27 was also, in all cases, more effective at inducing a faster and more intense apoptotic cascade than Paclitaxel. Because of recent findings that calcium flux through TRPV6 can initiate an anti-apoptotic response in cancer cells, that is communicated through the NFAT transcription factor circuit (Lehen'kyi et al. 2007) and that reduction in the amount of TRPV6 in the breast cancer cell line T 47D enhances the effect of a tamoxifen, a taxol (Bolanz et al. 2008), co-treatment with either of the C-peptides (or a combination of them) with any of the taxols would result in enhanced anti-cancer treatment.

Comparison of SorC13 and Paclitaxel in the human breast cancer cell line T 47D and the comparison of SorC27 and Paclitaxel in the human breast cancer cell line MCF 7 is illustrated in FIG. 4. There was more rapid induction of apoptosis by the SorC-peptides in these two cells lines, and greater intensity of the apoptosis cascade. Similar effects of earlier and more intense initiation of the apoptotic cascade by the two SorC-peptides were observed in MB 468 and MB231.

Example 5

Analysis of SorC13 and SorC27 with Paclitaxel in Enhancing the Induction of Apoptosis in Metastatic Human Breast Cancer Cell Lines To benchmark the effect of both C-type peptides with a gold-standard treatment presently used against breast cancer (Paclitaxel), combinations of SorC13 (10 and 100 uM), SorC27 (10 and 100 uM) and Paclitaxel (10 uM) are compared in human breast cancer cell lines MCF7 (from ATCC HTB-22 and T47D (from ATCC HTB-133). The cell lines are prepared as per ATCC methods. Both the APO-ONE assay (Promega) and the CellTiter Blue are used on the panel of breast cancer cell lines. The treatment groups are as follows: (n=8 per treatment)
1) No Treatment (Control)
2) Treat with Paclitaxel (10 uM)
3) Treat with 2 doses SorC13 (10, 100 uM)
4) Treat with 2 doses SorC27 (10, 100 uM)
5) Treat with single dose Paclitaxel (10 uM) and 2 doses SorC13 (10, 100 uM)
6) Treat with single dose Paclitaxel (10 uM) and 2 doses SorC27 (10, 100 uM)

The data are compared directly in terms of mean response and tested for significant difference.

The combination of either SorC27 or SorC13 with Paclitaxel has a greater effect inducing apoptosis in human breast cancer cell lines than either of the treatments alone. These results are measured as an Apoptotic Index (treatment response/control response; AI=1 when there is no effect) and by determining whether cell viability decreased (+) or not (−).

Example 6

Analysis of SorC13 and SorC27 Against the Paclitaxel/Carboplatin Cocktail in Induction of Apoptosis in Metastatic Human Ovarian Cancer Cell Lines To compare the effect of the two SorC-peptides against the gold-standard treatment for ovarian cancers SorC13 or SorC27 was compared to treatment with a carboplatin and taxol (CAT) cocktail (10 uM Paclitaxel, 20 mM carboplatin) using the APO-ONE assay, which measures the combined activities of caspase 3 and caspase 7. Because of the mixed treatment (CAT), the effects were compared in terms of the ratio of treatment:control. If no effect was noted then the ratio=1. Comparisons of the treatment:control ratios were examined with the Student's t-test at a confidence level of 95%. Ratios of larger than a value of unity indicated a positive effect. The effects are illustrated in FIG. 5. A concentration effect of SorC27 on one of the ovarian cell lines is presented in FIG. 6. These Figures illustrate that:
  SorC27 (10 uM and 100 uM) produced apoptosis sooner and more intensely than the CAT cocktail in SKOV3, OVCAR3 and was similar to the CAT in CaOV3 and OV90.
  SorC13 produced earlier and more intense apoptosis cascade than the CAT cocktail for SKOV3, CaOV3, OVCa3 and OV90.

Example 7

Analysis of SorC13 or SorC27 with the Paclitaxel/Carboplatin Cocktail in Enhancing the Induction of Apoptosis In Metastatic Human Ovarian Cancer Cell Lines To compare the effect of the two C-peptides against the gold-standard treatment for ovarian cancers SorC13 and SorC27 are compared to treatment with a carboplatin and taxol (CAT) cocktail (10 uM Paclitaxel, 20 mM carboplatin) using the APO-ONE assay. Two human ovarian adenocarcinoma tumor cell lines, SKOV3 (from ATCC HTB-77) and NIH:OVCAR-3 (from ATCC HTB-161) are used and prepared as per ATCC methods. Because of the mixed treatment (CAT), the effects are compared in terms of the ratio of treatment:control. If no effect is noted then the ratio=1. Comparisons of the treatment:control ratios are examined. Ratios of larger than a value of unity indicate a positive effect. The treatment groups are as follows:

(n=8 per treatment)

1) No Treatment (Control)
2) Treat with Paclitaxel (10 uM)
3) Treat with 2 doses SorC13 (10, 100 uM)
4) Treat with 2 doses SorC27 (10, 100 uM)
5) Treat with single dose Paclitaxel (10 uM) and 2 doses SorC13 (10, 100 uM)
6) Treat with single dose Paclitaxel (10 uM) and 2 doses SorC27 (10, 100 uM)

The data are compared directly in terms of mean response. The combination effects of SorC27+Paclitaxel and SorC13+Paclitaxel on one of the ovarian cell lines show that:

SorC27 (10 uM and 100 uM) in combination with CAT cocktail enhance apoptosis sooner and more intensely than either treatment alone in SKOV3 and NIH:OVCAR-3 ovarian cancer cell lines.

SorC13 (10 uM and 100 uM) in combination with CAT cocktail enhance apoptosis sooner and more intensely than either treatment alone in SKOV3 and NIH:OVCAR-3 ovarian cancer cell lines.

These results are measured as an Apoptotic Index (treatment response/control response; AI=1 when there is no effect) and by determining whether cell viability decreased (+) or not (−).

Example 8

Tissue Distribution of SorC13 and SorC27

SorC13 and SorC27 were labeled with the near-infrared probe, Cy5.5. SorC13 was labeled at lysine-1 and lysine-8 with the infrared fluorescent probe cy5.5 through reaction with Cy5.5 NHS ester-activated process. SorC27 was labeled at the single cysteine thiol with Cy5.5 maleamide-activated reaction. The labeled peptides were purified with a combination of size exclusion chromatography and HPLC. The label, Cy5.5, fluoresces in the infra-red region after excitation with a scanning laser. The low energy laser is able to penetrate the animal to about 1 cm and, thus, by scanning prone and supine positions, the presence of the tagged peptides can be quantified in three dimensions.

Figure 8:
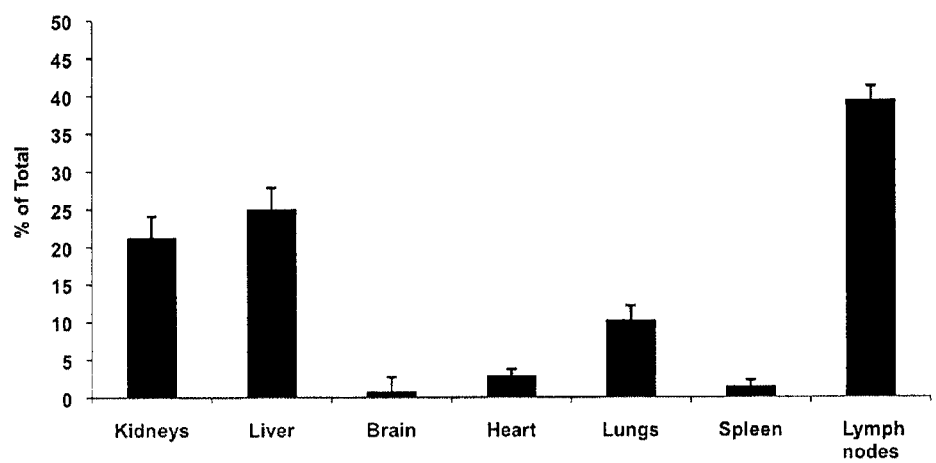
FIG. 8 shows the distribution of Cy5.5 labeled SorC13 in CD1 mice 4 hours after i.v. injection. The Y-axis is the percentage of total fluorescence measured in all tissues.
Figure 9:
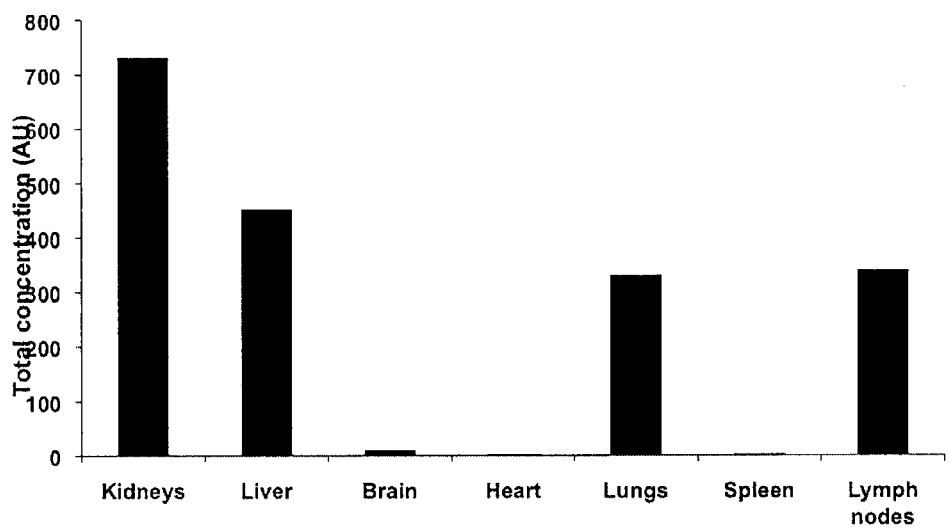
FIG. 9 shows the distribution of Cy5.5 labeled SorC27 in CD1 mice 4 hours after i.v. injection. The Y-axis is the total fluorescence measured in each tissue.

Cy5.5-labeled peptides were intravenously injected into CD1 mice (4 for each compound) at 100 ug per animal in 100 uL, and animals were imaged live using an optical imaging system, Optix eXplorer (GE Healthcare Systems) at different time points (30 min, 90 min, 4 h). Some animals were observed at 24 hours after perfusion to remove blood (and lymph). The bio-distribution of the labeled peptides in different organs and tissues were visualized and relatively quantified by optical imaging analysis. This protocol allows for visualization of the location of the labeled peptides and how the location changes over time. FIG. 7 shows the location of lymph nodes in the mouse. Nodes that accumulated the labeled peptides are indicated by line 1 (superfacial cervical nodes), line 4 (axillary nodes), line 5 (brachial nodes), line 8 (mesenteric nodes) and line 9 (inguinal nodes). FIGS. 8, 9 and 10 show the amounts of labeled peptides in various organs ex vivo. Combined, these experiments show that:

Neither of the C-peptides moved across the blood-brain barrier.

Tagged SorC13 and SorC27 localize predominantly in lymph nodes, lung, liver and kidney.

Tagged SorC13 and SorC27 were still detectable in these tissues after perfusion at 24 hours.

Measurement of the fluorescence life-time in various organs showed that metabolism of labeled peptides appears to be in liver and kidney as Cy5.5 has a shorted life-time than peptide/Cy5.5 adducts.

Example 9

SorC13 and SorC27 Induce Apoptosis in Human Non Small Cell Lung Carcinoma (NSCLC) Tumor Cells The effects of the C-peptides on metastasizing human lung carcinoma cells are studied. The tissue distribution data described above indicated that the C-peptides accumulate in the lung and localize in the lymph nodes. In vitro studies employing SorC13 and SorC27 are carried out in metastatic lymph node-derived cell lines to determine their effect on Human Non-Small Cell Lung Carcinoma (NSCLC) lines H1437 (from ATCC CRL-5872) and H2087 (from ATCC CRL-5922). Both of these cell lines are adenocarcinomas derived from the metastaic site (lymph node) and from a stage 1 NSCLC lung cancer. Major lymphatics of interest which are usefully treated with peptides of the invention include superfacial cervical nodes, axillary nodes, brachial nodes, mesenteric nodes and inguinal nodes.

For the study, the cell lines are grown under the recommended conditions and in culture media recommended by ATCC. The cell lines are cultured under sterile conditions at 37° C., in a humidified 5% $CO_2$ atmosphere.

Both the APO-ONE assay and the CellTiter Blue (Promega) are used on the cell lines to evaluate apoptosis and cell viability, respectively. The treatment groups are as follows:

1) No Treatment
2) Treat with 2 doses SorC13 (10 and 100 uM)
3) Treat with 2 doses SorC27 (10 and 100 uM)

The data are compared directly in terms of mean response. SorC27 and SorC13 induce apoptosis in human metastatic NSCLC lines.

Examples 10-13

The Effects of the C-Peptides are Evaluated in a Variety of Human Cancer Cell Lines The effects of SorC13 and SorC27 treatment on a number of cancer cell lines are tested in vitro. As described above, the C-peptides induced apoptosis in both breast and ovarian cancer cell lines. The C-peptides also demonstrate the ability to induce apoptosis and decrease cell viability in other cancer cells in vitro. In the following Examples 10-13, SorC13 and SorC27 are assessed for their ability to induce apoptosis in a selected variety of human cancer lines. They include: PC3, human chronic myelogenous leukemia (CML) K-562, human acute myelogenous leukemia (AML) MV-4-11, Burkitt's Lymphoma cell line Daudi.

For this work, the concentrations of SorC13 and SorC27 used are 0 uM, 10 uM and 100 uM. The experiments extend over a 5 to 7 day period. All measurements are done in quadruplicate with both a blank (no cells) and control (vehicle, no peptide) used to correct the test measurements. The time-response data, and the dose-response data are plotted as means±standard error of the mean.

Example 10

The C-Peptides Induce Apoptosis in Human Prostate Cancer Cell Lines

The cell lines PC3 (from ATCC CRL-1435) and LnCaP clone FGC (from ATCC CRL-1740), obtained from the American Type Culture Collection (ATCC) and grown under the recommended conditions and in culture media recommended by ATCC. The cell lines are cultured under sterile conditions at 37° C., in a humidified 5% $CO_2$ atmosphere.

Induction of apoptosis and attendant decrease is observed in cell viability in the cancer cell lines. From the large increases in the activities of the caspase3/7 activity, it is clear that there is a time dependent effect and a dose dependent effect on the induction of apoptosis.

The observations of the effects of SorC13 and SorC27 on the cell line are:
SorC27 induces apoptosis and decreases cell viability;
SorC13 induces apoptosis and decreases cell viability.

Example 11

The C-Peptides Induce Apoptosis in Human Burkitt's Lymphoma Cell Lines

The cell line Daudi (from ATCC CCL-213) is grown under the recommended conditions and in culture media recommended by ATCC. The cell lines were cultured under sterile conditions at 37° C., in a humidified 5% $CO_2$ atmosphere.

Induction of apoptosis and attendant decrease is observed in cell viability in the cancer cell lines. From the large increases in the activities of the caspase3/7 activity, it is clear that there is a time dependent effect and a dose dependent effect on the induction of apoptosis.

The observations of the effects of SorC13 and SorC27 on the cell line are:
SorC27 induces apoptosis and decreases cell viability.
SorC13 induces apoptosis and decreases cell viability.

Example 12

The C-Peptides Induce Apoptosis in Human Chronic Myelogenous Leukemia (CML) Cell Line, K-562

The cell line K-562 (from ATCC CCL-243) is grown under the recommended conditions and in culture media recommended by ATCC. The cell lines were cultured under sterile conditions at 37° C., in a humidified 5% $CO_2$ atmosphere.

Induction of apoptosis and attendant decrease is observed in cell viability in the cancer cell lines. From the large increases in the activities of the caspase 3/7 activity, it is clear that there is a time dependent effect and a dose dependent effect on the induction of apoptosis.

The effects of SorC13 and SorC27 on the cell line are:
SorC27 induces apoptosis and decreases cell viability;
SorC13 induces apoptosis and decreases cell viability.

Example 13

The C-Peptides Induce Apoptosis in Human Acute Myelogenous Leukemia (AML) Cell Line, MV-4-11

The cell line MV-4-11 (from ATCC DRL-9591) is grown under the recommended conditions and in culture media recommended by ATCC. The cell lines were cultured under sterile conditions at 37° C., in a humidified 5% $CO_2$ atmosphere.

Induction of apoptosis and attendant decrease is observed in cell viability in the cancer cell lines. From the large increases in the activities of the caspase3/7 activity, it is clear that there is a time dependent effect and a dose dependent effect on the induction of apoptosis.

The observations of the effects of SorC13 and SorC27 on the cell line are:
SorC27 induces apoptosis and decreases cell viability;
SorC13 induces apoptosis and decreases cell viability.

Examples 14-20

The SorC-Peptides have Anti-Tumor Activity In Vivo

In vivo studies (Examples 14-20) employing the C-peptides in a xenograft model are conducted to evaluate the response of xenografts of human cancer cell lines in a rodent (mouse) model to treatment. The S or C peptides have anti-tumor activity in vivo.

The cell lines used to model human breast cancer and human ovarian cancer are obtained from the American Type Culture Collection (ATCC) and grown under the recommended conditions and in culture media recommended by ATCC. The cell types, ATCC catalogue number and cell line description are listed in Table 8.

TABLE 8

| | Description of ATCC Cell Lines |
|---|---|
| NIH-OVCAR-3 (ATCC HTB-161) | The NIH: OVCAR-3 line was established in 1982 by T. C. Hamilton, et al. from the malignant ascites of a patient with progressive adenocarcinoma of the ovary. The cell line is resistant to clinically relevant concentrations of adriamycin, melphalan and cisplatin. Xenograft models have been used to show that treatment with 17 beta estradiol induces progesterone receptors in this human ovarian carcinoma. NIH: OVCAR-3 is an appropriate model system in which to study drug resistance in ovarian cancer, and the presence of hormone receptors is useful for the evaluation of hormonal therapy (from ATCC HTB-161). TRPV6 mRNA is expressed (the trpv6 genes are turned on) in this ovarian cell line. |

TABLE 8-continued

Description of ATCC Cell Lines

| | |
|---|---|
| SKOV3 (ATCC HTB-77) | SKOV3 cells from the malignant ascites of a patient with progressive adenocarcinoma of the ovary.<br>This cell line is resistant to tumor necrosis factor and to several cytotoxic drugs including diphtheria toxin, cis-platinum and adriamycin (from ATCC HTB-77).<br>TRPV6 mRNA is expressed (the trpv6 genes are turned on) in this ovarian cell line. |
| Daudi: Burkitt's Lymphoma (ATCC CCL-213) | The Daudi line was derived from a 16-year-old male with Burkitt's lymphoma by E. Klein and G. Klein in May, 1967.<br>The cells are negative for beta-2-microglobulin.<br>They are positive for EBNA, VCA and Surface immunoglobulin (sIg+).<br>The Daudi is a well characterized B lymphoblast cell line which has been employed extensively in studies of mechanisms of leukemogenesis. (from ATCC CCL-213) |
| Human chronic myelogenous leukemia (CML) cell line, K-562 (ATCC CCL-243) | The continuous cell line K-562 was established by Lozzio and Lozzio from the pleural effusion of a 53-year-old female with chronic myelogenous leukemia in terminal blast crises. [PubMed: 163658].<br>Studies conducted by Anderson, et al., on the surface membrane properties showed that the K-562 was a human erythroleukemia line.<br>The cell line is tumorigenic in nude mice. (Tumors developed within 21 days at 100% frequency (5/5) in nude mice inoculated subcutaneously with $10^7$ cells) (from ATCC CCL-243). |
| Human acute myelogenous leukemia (AML) cell line, MV 4-11 (ATCC CRL 9591) | The MV4-11 cell line was established by Rovera and associates from the blast cells of a 10-year-old male with biphenotypic B-myelomonocytic leukemia.<br>This line was formerly designated ATCC HTB-189. (from ATCC CRL-9591). |
| Human prostate cancer LnCaP clone FGC (ATCC CRL-1740) | LnCaP clone FGC was isolated in 1977 by J. S. Horoszewicz, et al., from a needle aspiration biopsy of the left supraclavicular lymph node of a 50-year-old Caucasian male (blood type B+) with confirmed diagnosis of metastatic prostate carcinoma.<br>They attach only lightly to the substrate, do not become confluent and rapidly acidify the medium.<br>Growth is very slow.(from ATCC CRL-1740). |
| Human prostate adenocarcinoma cell line PC3 (ATCC CRL-1435) | The PC-3 was initiated from a bone metastasis of a grade IV prostatic adenocarcinoma from a 62-year-old male Caucasian.<br>Tumors developed within 21 days at 100% frequency (5/5) in nude mice inoculated subcutaneously with 10(7) cells.<br>The cells exhibit low acid phosphatase and testosterone-5-alpha reductase activities. (from ATCC CRL-1435). |
| Human breast cancer cell line MCF7 (ATCC HTB-22) | Derived from a metastatic site as a pleural effusion.<br>The primary tumour derived from breast in a patient with epithelial adenocarcinoma.<br>The MCF7 line retains several characteristics of differentiated mammary epithelium including ability to process estradiol via cytoplasmic estrogen receptors and the capability of forming domes.<br>The cells express the WNT7B oncogene [PubMed: 8168088].<br>Contains the Tx-4 oncogene.<br>Growth of MCF7 cells is inhibited by tumor necrosis factor alpha (TNF alpha). Secretion of IGFBP's can be modulated by treatment with anti-estrogens. (ATCC# HTB-22) |
| Human breast cancer cell line MDA-MB-231 (ATCC HTB-26) | Derived from a metastatic site as a pleural effusion.<br>The primary tumour derived from breast in a patient with epithelial adenocarcinoma. The cells express the WNT7B oncogene.<br>MDA-MB-231 cells express low levels of HER2. (from ATCC HTB-26). |

Example 14

Anti-Tumor Activity of SorC13 and SorC27 Alone and in Combination with CAT (Carboplatin and Paclitaxel Cocktail) Against Human Ovarian Adenocarcinoma Tumor Cells in a Mouse Xenograft Model The human ovarian adenocarcinoma cell lines, SKOV3 (ATCC #HTB-77) and NIH:OVCAR-3 (ATCC #HTB-161), are cultured in growth media prepared with ATCC complete growth medium.

Cell Cultures
SKOV3 Cell Line

The base medium for the SKOV3 line is ATCC-formulated McCoy's 5a Medium Modified (ATCC Catalog No. 30-2007). To make the complete growth medium, the following components are added to the base medium: fetal bovine serum to a final concentration of 10% at 37° C. (air, 95%; carbon dioxide ($CO_2$), 5%). The sub-culturing protocol of ATCC for SKOV3 cell cultures is followed.

NIH-OVCAR-3 Cell Line

The base medium for the NIH-OVCAR-3 cell line is ATCC-formulated RPMI-1640 Medium (ATCC Catalog No. 30-2001). To make the complete growth medium the ATCC propagation protocol for NIH-OVCAR-3 cell cultures is followed.

Cell Preparation

Cells that have cryo-preserved in liquid nitrogen are rapidly thawed at 37° C. and transferred to a tissue culture flask containing growth media and then incubated at 37° C. in a 5% $CO_2$ incubator. To expand the cell line, cultures are passaged 1:2 to a density of $5\times10^6$ cells/ml every three days by adding an equal volume of fresh growth media. When the flasks reach a density of approximately $10\times10^6$ cells/ml, the above passaging process is repeated until sufficient cells are obtained for implantation into mice.

Seven to eight week old, female NOD/SCID mice were housed 4-5/cage in micro-isolators, with a 12 hr/12 hr light/dark cycle, acclimated for at least 1 week prior to use and fed normal laboratory chow ad libitum. Studies were conducted on animals that were between 8 and 12 weeks of age at the time of tumor cell implantation.

Formulation Procedures
SorC13/SorC27

To formulate SorC13 and SorC27, stock solutions of the test article are prepared by dissolving the appropriate amounts of the compound in physiologically buffered saline (pH 7.0 to 7.4 at 25° C.) to comprise a final solution to deliver 10 and 100 mg/Kg mouse. Stock solutions are prepared weekly, stored at −20° C. and diluted fresh each day for dosing. All solutions are filter sterilized with a 0.22 mu filter prior to further manipulation. The filter sterilizer units were pre-washed with a small volume of sterile distilled water.

Carboplatin/Paclitaxel (CAT) Reference Solution

Stock solutions are prepared containing 20 mM and 10 uM of carboplatin and Paclitaxel, respectively. Carboplatin and Paclitaxel are obtained from Sigma-Aldrich. All solutions are filter sterilized with a 0.22 mu filter prior to further manipulation.

Implantation Procedures

Optionally, to implant NIH-OVCAR-3 or SKOV3 tumor cells into NOD/SCID mice, cell cultures are centrifuged to pellet the cells, the supernatant is aspirated, the cell pellet is resuspended in 10 ml of growth media and the cell number is determined using a hemocytometer. The cells are then washed in appropriate media and re-suspended at a concentration of $5\times10^7$ cells/ml in media. Using a 27 gauge needle and 1 cc syringe, 0.1 ml of the cell suspension is injected subcutaneously into the flanks of the mice. Tumors are then permitted to develop in vivo until the majority reach 100-200 $mm^3$ in tumor volume, which typically requires 1-2 weeks following implantation. These tumors are used to produce tissue subcutaneous implants into NOD/SCID mice which after 2 days are treated with either the test peptides or CAT.

The following groups are typically included:
1) Mice with tumor implants receiving vehicle;
2) Mice with tumor implants receiving the reference compound CAT;
3) Mice with tumor implants receiving dose 1 of SorC13;
4) Mice with tumor implants receiving dose 1 of SorC27;
5) Mice with tumor implants receiving dose 1 of SorC13 and CAT;
6) Mice with tumor implants receiving dose 1 of SorC27 and CAT.

Measurements

Animals with oblong, very small or large tumors are discarded, and only animals carrying tumors that displayed consistent growth rates are selected for studies. Tumor volumes (V) are calculated by caliper measurement using standard measurements of the width (W), length (L) and thickness (T) of tumors. Animals are randomized into treatment groups so that the median tumor volumes of each group were similar at the start of dosing. % T/C values, as a measure of efficacy, are determined where C refers to volume of control or untreated tumor, and T refers to volume of treated tumor.

Treatment Procedures

Animals are intraperitoneally (i.p.) injected with this formulation at 10 ml per kg body weight on a schedule.

Results

Treatment with a dose of 400 mg/kg body weight of SorC13 and SorC27 substantially decreases the growth rate of NIH-OVCAR-3 and SKOV3 cells in NOD/SCID mice. This effect is not associated with toxicity, as shown by stable body weight and lack of stress symptoms (diarrhea, panting, ruffled fur)

Experimental Results with SKOV3 Cells and SorC27

SKOV3 cells were obtained from ATCC, cultured and expanded to suitable numbers to establish xenografts in mice and then formulated into gel pellets and grafted under the renal capsule of surrogate NOD/SCID mice in order to establish the tumors. Tumors are then permitted to develop in vivo until the majority reach 100-200 $mm^3$ in tumor volume, which typically requires 1-2 weeks following implantation. Once xenografts are established, they are harvested and cut into multiple uniform pieces. Sixteen to eighteen pieces were implanted subcutaneously into each NOD/SCID mouse for experimentation. After 2 days, the animals are treated with either the test peptides or CAT or combinations.

Figure 12:
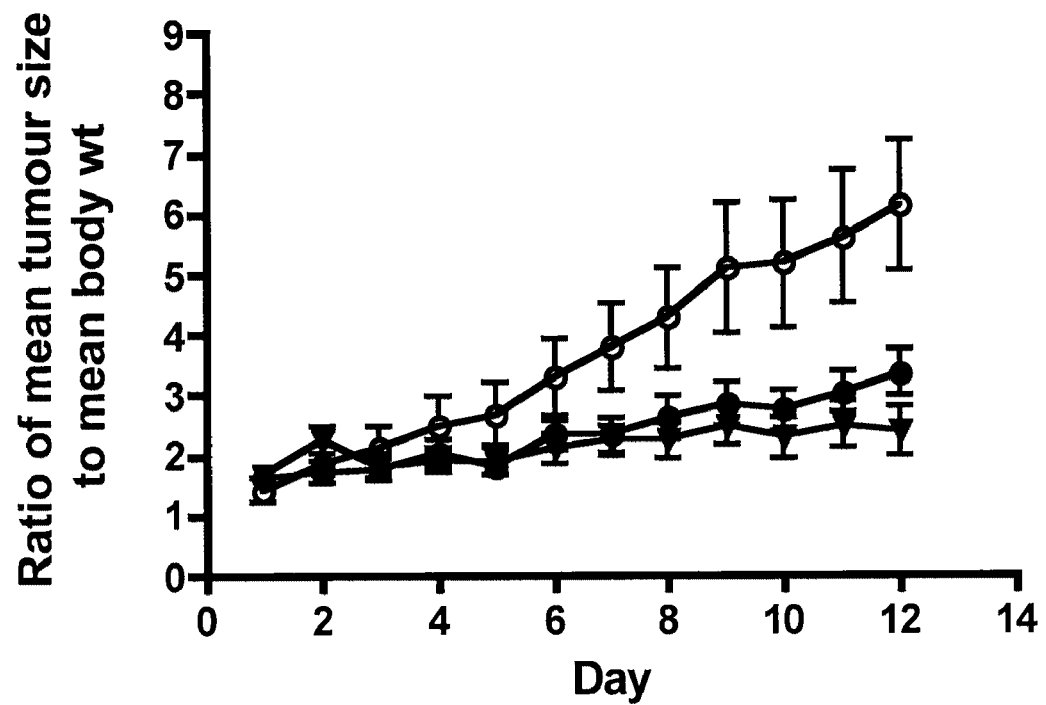
FIG. 12 shows results from an in vivo experiment with NOD/SCID mice xenografted with human SKOV3 ovarian cancer tumors. Mice were injected with either control saline, SorC27 or a mixture of Paclitaxel and Carboplatin (CAT). SorC27 reduced the tumor volume significantly (p<0.05) when compared to a control saline injection and was not distinguishable from mice treated with CAT, over 12 days when tumor size was normalized to body weight.

Mice implanted with SKOV3 cells as detailed above received saline (control), SorC27 (400 mg/kg), by i.p. injection every day for 12 days or CAT injections one every week. The tumor volume and body weights were measured every day. As well, general health of the animals was monitored every day. The results shown in FIG. 12 are presented in terms of tumor load normalized to body weight. Both SorC27 and CAT treatments showed greatly reduced tumor volume and were significantly different than Control. % T/C ratio (mean tumour volume of treated/mean tumour volume of control) was 39.9%, reflecting a 60.1% decrease in tumour growth. By Day 12 there was no statistically significant difference between CAT and SorC27 at this dose.

Example 15

Anti-Tumor Activity of SorC13 and SorC27 Alone and in Combination with Paclitaxel Against Human Breast Cancer Cells in a Mouse Xenograft Model The human breast cancer cell lines, MCF7 (ATCC #HTB-22) and T47D (ATCC #HTB-133), are cultured in growth media prepared with ATCC complete growth medium.

Cell cultures, cell preparation, animal procedures, SorC13/SorC27 formulation procedures, implantation procedures, measurements and treatment procedures are as described in Example 14.

The following groups are typically included:
1) Mice with tumor implants receiving vehicle;
2) Mice with tumor implants receiving the reference compound Paclitaxel;
3) Mice with tumor implants receiving dose 1 of SorC13;
4) Mice with tumor implants receiving dose 1 of SorC27;
5) Mice with tumor implants receiving dose 1 of SorC13 and Paclitaxel;
6) Mice with tumor implants receiving dose 1 of SorC27 and Paclitaxel.

Formulation Procedures
Paclitaxel Reference Solution

Stock solutions are prepared containing 10 uM of Paclitaxel. Paclitaxel is obtained from Sigma-Aldrich.

Results

Treatment with a dose of SorC13 or SORC27, optionally 200-400 mg/kg body weight, substantially decreases the growth rate of MCF7 and T47D cells in NOD/SCID mice, with a % T/C value of <100%. This effect is not associated with toxicity, as shown by reduced % T/C over the course of the study.

Example 16

Anti-Tumor Activity of SORC13 and SORC27 Against Human Chronic Myelogenous Leukemia (CML) Tumor Cells, [K-562 (ATCC #CCL-243)] in a Mouse Xenograft Model The human chronic myelogenous leukemia (CML) cell line, K-562 (ATCC #CCL-243) is obtained from the American Type Culture Collection. The cells are cultured in growth media prepared with ATCC complete growth medium.

Cell Cultures

The base medium for the K-562 line is ATCC-formulated Iscove's Modified Dulbecco's Medium, Catalog No. 30-2005. To make the complete growth medium, the following components are added to the base medium: fetal bovine serum to a final concentration of 10%. To make the complete growth medium, the ATCC propagation protocol for K-562 cell cultures is be followed.

The following groups are typically included:
1) Mice with tumor implants receiving vehicle;
2) Mice with tumor implants receiving dose 1 of SORC13;
3) Mice with tumor implants receiving dose 1 of SORC27;

Cell preparation, animal procedures, SorC13/SorC27 formulation procedures, implantation procedures, measurements and treatment procedures are as described in Example 14.

Results

Treatment with a dose of SorC13 or SORC27, optionally 200-400 mg/kg body weight, substantially decreases the growth rate of K-562 cells in NOD/SCID mice, with a % T/C value of <100. This effect is not associated with toxicity.

Example 17

Anti-Tumor Activity of SorC13 and SorC27 Against Human Prostate Cancer Tumor Cells, LnCaP Clone FGC in a Mouse Xenograft Model The human prostate cancer cell line, LnCaP clone FGC (from ATCC CRL-1740) is obtained from the American Type Culture Collection. The cells are cultured in growth media prepared with ATCC complete growth medium.

Cell Cultures

The base medium for the LnCaP clone FGC line is ATCC-formulated.

Animal Procedures

As described in Example 14.

The following groups are typically included:
1) Mice with tumor implants receiving vehicle;
2) Mice with tumor implants receiving dose 1 of SorC13;
3) Mice with tumor implants receiving dose 1 of SorC27.

Cell preparation, SorC13/SorC27 formulation procedures, implantation procedures, measurements and treatment procedures are as described in Example 14.

Results

Treatment with a dose of SorC13 or SORC27, optionally 200-400 mg/kg body weight, substantially decreases the growth rate of LnCaP cells in SCID mice, with a % T/C value of <100. This effect is not associated with toxicity, as shown by reduced % T/C over the course of the study.

Example 18

Anti-Tumor Activity of SorC13 and SorC27 Against Human Breast Cancer Tumor Cells, MCF7 in a Mouse Xenograft Model The human breast cancer cell line, MCF-7 (from ATCC HTB-22) is obtained from the American Type Culture Collection. The cells are cultured in growth media prepared with ATCC complete growth medium.

Animal Procedures

As described in Example 14.

The following groups are typically included:
1) Mice with tumor implants receiving vehicle;
2) Mice with tumor implants receiving dose 1 of SorC13;
3) Mice with tumor implants receiving dose 1 of SorC27;

Cell culture, cell preparation, SorC13/SorC27 formulation procedures, implantation procedures, measurements and treatment procedures are as described in Example 14.

Results

Treatment with a dose of SorC13 or SORC27, optionally 200-400 mg/kg body weight, substantially decreases the growth rate of MCF7 cells in NOD/SCID mice, with a % T/C value of <100. This effect is not associated with toxicity, as shown by reduced % T/C over the course of the study.

Example 19

Anti-Tumor Activity of SorC13 and SorC27 Against Human Breast Cancer Tumor Cells, MDA-MB-231 in a Mouse Xenograft Model The human breast cancer cell line, MDA-MB-231 (from ATCC HTB-26) is obtained from the American Type Culture Collection. The cells are cultured in growth media prepared with ATCC complete growth medium.

Cell Cultures

The base medium for the MDA-MB-231 cell line is ATCC-formulated Leibovitz's L-15 Medium, Catalog No. 30-2008. To make the complete growth medium, the following components are added to the base medium: fetal bovine serum to a final concentration of 10%. To make the complete growth medium, the ATCC propagation protocol for MDA-MB-231 cell cultures is followed.

Animal Procedures

As described in Example 14

The following groups are typically included:
1) Mice with tumor implants receiving vehicle;
2) Mice with tumor implants receiving dose 1 of SorC13;
3) Mice with tumor implants receiving dose 1 of SorC27;

Cell preparation, SorC13/SorC27 formulation procedures, implantation procedures, measurements and treatment procedures are as described in Example 14.

Results

Treatment with a dose of SorC13 or SORC27, optionally 200-400 mg/kg body weight, substantially decreases the growth rate of MDA-MB-231 cells in SCID mice, with a % T/C value of <100. This effect is not associated with toxicity, as shown by reduced % T/C over the course of the study.

Example 20

Anti-Tumor Activity of SorC13 and SorC27 Against Human Acute Myelogenous Leukemia (AML) Tumor Cells, MV-4-11 in a Mouse Xenograft Model The human breast cancer cell line, MV-4-11 (from ATCC CRL-9591) is obtained from the American Type Culture Collection. The cells are cultured in growth media prepared with ATCC complete growth medium.

Cell Cultures

The base medium for the MV-4-11 cell line is ATCC-formulated Iscove's Modified Dulbecco's Medium, Catalog No. 30-2005. To make the complete growth medium, the following components are added to the base medium: fetal bovine serum to a final concentration of 10%. To make the complete growth medium, the ATCC propagation protocol for MV-4-11 cell cultures is followed.

Animal Procedures

As described in Example 14.

The following groups are typically included:
1) Mice with tumor implants receiving vehicle;
2) Mice with tumor implants receiving dose 1 of SorC13;
3) Mice with tumor implants receiving dose 1 of SorC27;

Cell preparation, SorC13/SorC27 formulation procedures, implantation procedures, measurements and treatment procedures are as described in Example 14.

Results

Treatment with a dose of SorC13 or SORC27, optionally 200-400 mg/kg body weight, substantially decreases the growth rate of MV-4-11 cells in SCID mice, with a % T/C value of <100. This effect is not associated with toxicity, as shown by reduced % T/C over the course of the study.

Example 21

Detection and Detection Limits of the C-Peptides

Reversed-phase HPLC was used to detect and quantify SorC13 and SorC27. A Phenomenex Gemini, 5 u, C-18 reversed-phase column, (250×4.60 mm) was used for analytical procedures. The solvent system was a gradient of acetonitrile and water, each containing 0.1% v/v trifluoroacetic acid. HPLC was conducted at a column temperature of 30.0° C. The solvent system was a 10% to 60% acetonitrile (0.1% TFA) gradient with 90% to 40% water (0.1% TFA) over 40 minutes, at a flow rate of 1.0 mL/min. Detection was at 224 nm. Retention times for the peptides were 11.5 min and 14.7 min for SorC13 and SorC27 respectively.

The quantification and detection limits of SorC13 and SorC27 in water were determined by sequentially diluting solutions containing known masses of pure peptides and submitting to HPLC analysis. In the case of quantifying the two C-peptides in rat or human plasma the process required pretreatment to eliminate proteolytic activity from the plasma samples. A combination of the addition of Pefabloc (Sigma-Aldrich; a protease inhibitor) at 2 uL of 2 mM Pefabloc per 100 uL solution and centrifugation in an Amicon YM-10 Centricon size-exclusion filter (MWCO 10 kDa) to remove proteolytic enzymes provided a peptide-stable medium. All quantification experiments were done in triplicate and analyzed by calculating the best-straight line equation at the 95% confidence level.

Standard curves in all three media fit to a linear model within at the 95% (or greater) confidence level. The lower detection limits of SorC13 and SorC27 in all media under these conditions were at least 1 ug in a sample injection volume of 94 uL. Decrease in detection limits for these peptides is easily achieved with pre-analysis derivization for either colorimetric and fluorometric methods. Additionally, decreasing the wavelength of detection (e.g. 204 nm) also decreases the detection limit of the peptides.

Example 22

Degradation Rate of C-Peptides in Rat and Human Plasma

Rat plasma was obtained from blood taken from sacrificed rats (Sprague-Dawley) and placed into heparinized glass vials to prevent clotting. Whole blood was centrifuged at 8000×g for 5 minutes to spin down the cells leaving the plasma as supernatant. Human whole blood samples from healthy humans were taken in lithium-heparinized vacuum tubes. The samples were placed into 2.0 mL microcentrifuge tubes and centrifuged at 8000×g for 5 min. The plasma was carefully separated from red blood cells and used immediately.

Determination of degradation rate of the C-peptides was done by measuring, with the HPLC protocol, the amount of either SorC13 or SorC27 in dosed plasma samples, after time. Sample tubes (500 uL) containing 2 uL of 2 mM Pefabloc were previously prepared for sample delivery SorC13 (1.0 mg) or SorC27 (2.0 mg) were dissolved in 1.0 mL of fresh plasma (37° C.) and placed in an incubating water bath at 37° C. A sample (100 uL) was taken immediately and quenched in sample tubes containing 2 uL of 2 mM Pefabloc, mixed vigorously and immediately frozen at −80° C. This initial sample represented time zero for the run. At successive time intervals of 5 minutes, 100 uL samples were withdrawn, quenched in Pefabloc, mixed, and frozen at −80° C. until analysis.

Figure 11:
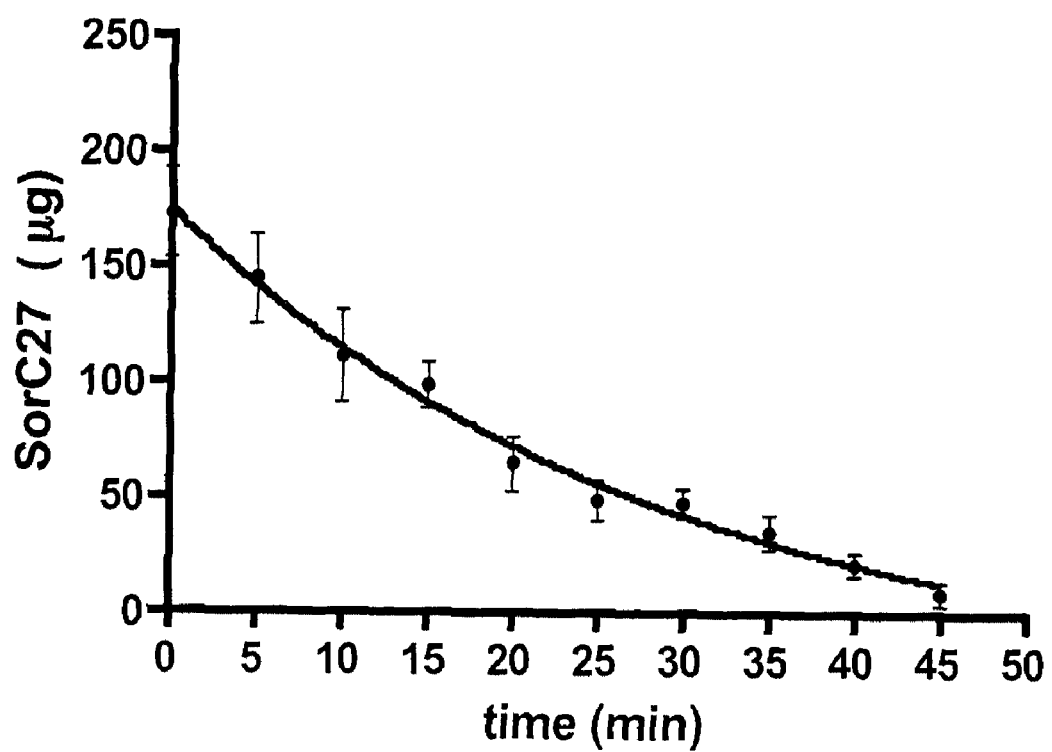
FIG. 11 shows degradation of SorC27 in human blood plasma from HPLC analysis of 100 ul of plasma diluted in 100 ul of 2 M KCl, 94 ul injection. The Y-axis indicates the amount (ug) of SorC27 in plasma prior to diluting with KCl, Half-Life=20.0 min, r=0.87, p<0.05. The data are mean±SEM, n=6.

The rat plasma degradation rate was determined for the plasma from three different rats, while the rate of degradation in human plasma used six separate plasma samples. The data used were the means (±SEM) and were fitted to a simple one-phase exponential decay model to determine the half-life of the two peptides. This also allowed the calculation of a static degradation rate. FIG. 11 is illustrative of the rate at which SorC27 was degraded in human plasma. Similar analysis for the two peptides in both plasma types showed:

SorC27 degraded with a half-life of 21 min in rat plasma and 20 min in human plasma SorC13 degraded with a half-life of 58 min in rat plasma and 56.6 min in human plasma Example 23

Toxicity Studies of SorC13 and SorC27

Acute Toxicity of SorC13 and SorC27

A single dose acute intravenous bolus injection toxicity study followed by a 5-day observation period in CD-1 mice was performed as described below. Three doses of each of SorC13 and SorC27 were used (10, 100 and 500 mg/Kg). Daily cage-side exams for 5 days with hourly exams for the first 4 hrs post injection. As part of the analysis the following assessments were made: body weights prior to dosing and at termination; all animals were necropsied (including preparation of bone marrow smears); organ weights were taken of all animals.

After in vivo i.v. injection into CD1 mice, SorC27 resulted in no change in blood pressure or heart rate over a 1 hour measurement period. There were no also neurological/behavioral changes over 72 hours. After in vivo i.v. injection into CD1 mice, SorC13 caused a small spike (approximately 25%) in blood pressure in the first 15 min which disappeared by 1 hour. There were no neurological/behavioral changes in the mice over 72 hours. Single intravenous injection of SorC13 or SorC27 into CD1 mice at doses of 10 mg/kg, 100 mg/kg and 500 mg/kg resulted in no adverse events over a 5 day post-injection observation period. In this latter experiment, necropsy showed no significant changes in all major organ systems. Also, a multiple dose of SorC27 at 400 mg/kg (i.p.) each day for 12 days in mice showed no indication of toxicity.

Repeated Dose Toxicity Study

In order to investigate repeated dose toxicity, SorC27 at 400 mg/kg formulated in saline was injected (i.p.) into NOD/SCID mice every day for 12 days. The animals were observed cage-side each day and examined at the end of the experimental period. Comparisons with control mice injected with saline alone showed no toxic effect, weight loss or change in organs on necropsy.

Example 24

The Pharmacokinetic (PK) Profiles of SorC13 and SorC27

A single dose acute intravenous bolus injection PK study is conducted using three doses of each of SorC13 and SorC27 (3 mg/Kg, 30 mg/Kg and 150 mg/Kg) using at least 3 mice per dosage group. Blood samples are taken at 6 time points: 5, 15 minutes, 1, 2 and 4 hrs post dose. Samples are then assayed for the presence of SorC13 or SorC27.

Results

The combination of clearance rate from the blood compartment plus enzymic degradation due to enzymes in plasma results in movement out of the blood compartment with a half-life less than 30 minutes.

Example 25

Comparison of the Presence of TRPV6 mRNA with Apoptotic Activity of C-Peptides in Different Cell Lines The presence of the mRNA for TRPV6 was tested using RT-PCR in each of the cell lines listed in Table 9. The TRPV6 primers (amplicon size ~400 by on agar gel) used were 5'-CTGCCTATGGAGCAAGTTCTG (forward primer) and 5'-TCAGATGTCATGGGCTCAAAG (reverse primer). The thermocycler program used for the amplification reaction was: 94° C. for 3 minutes; then, repeated for 30 cycles: 94° C. for 30 seconds, 53° C. for 30 seconds, 72° C. for 1 min 30 s 72° C. for 7 minutes. The amplification reactions were monitored by standard agar gel electrophoresis.

Results

Table 9 shows some a correspondence between the ability of the C-peptides to induce apoptosis in various breast and ovarian cancer cell lines and the presence of the mRNA for TRPV6. It is clear that those cell lines expressing the trpv6 gene, are susceptible to C-peptide induced apoptosis.

TABLE 9

Comparison of the expression of the trpv6 gene and induction of apoptosis by SorC13 and SorC27

| Cancer Type | Cell Line | TRPV6 mRNA (RT-PCR) | Apoptosis induced by C-peptides |
|---|---|---|---|
| Breast | MB 231 | (+) | (+) |
|  | MB 468 | (+) | (+) |
|  | T 47D | (+) | (+) |
|  | HCC1954 | (+) | (+) |
|  | MCF7 | (+) | (+) |
|  | MCF 10A | (−) | (−) |
|  | MCF 12A | (−) | (−) |
| Ovarian | OVCAR3 | (+) | (+) |
|  | OV C13 | (+) | Not Tested |
|  | SKOV-3 | (+) | (+) |
|  | OV 90 | Not Tested | (+) |
|  | OV 2008 | (+) | Not Tested |
|  | HEY C2 | (+) | (+) |

Other S or C peptides of the invention, such as SorC9 (HPSKVDLPR), are readily tested in protocols described in the above examples and shown to have in vitro and in vivo activity for inhibition of calcium activity with no paralytic activity. The peptides are also useful for preventing cell proliferation, inducing apoptosis and preventing or treating cancer.

Example 26

Anti-Tumor Activity of SorC13 in Combination with CAT Chemotherapy Against Ovarian Cancer Tumor Cells in a Mouse Xenograft Model In vivo studies employing a mouse xenograft model were conducted to evaluate the response of human ovarian cell line xenografts to combination therapies including low, medium or high doses of CAT chemotherapy (carboplatin and paclitaxel) and SorC13.

Cell Culture

SKOV3 Cell Line

The human ovarian adenocarcinoma cell line SKOV3 (ATCC #HTB-77) was cultured in growth media prepared with ATCC complete growth medium. The base medium for the SKOV3 line is ATCC-formulated McCoy's 5a Medium Modified (ATCC Catalog No. 30-2007). To make the complete growth medium, the following components were added to the base medium: fetal bovine serum to a final concentration of 10% at 37° C. (air, 95%; carbon dioxide ($CO_2$), 5%). The sub-culturing protocol of ATCC for SKOV3 cell cultures was followed.

Cell Preparation

Cells cryo-preserved in liquid nitrogen were rapidly thawed at 37° C. and transferred to a tissue culture flask containing growth media and then incubated at 37° C. in a 5% $CO_2$ incubator. To expand the cell line, cultures were passaged 1:2 to a density of $5 \times 10^6$ cells/ml every three days by adding an equal volume of fresh growth media. When the flasks reach a density of approximately $10 \times 10^6$ cells/ml, the above passaging process is repeated until sufficient cells are obtained for implantation into mice.

Seven to eight week old, female NOD/SCID mice were housed 4-5/cage in micro-isolators, with a 12 hr/12 hr light/dark cycle, acclimated for at least 1 week prior to use and fed normal laboratory chow ad libitum. Studies were conducted on animals that were between 8 and 12 weeks of age at the time of tumor cell implantation. Animals were handled under standard sterile conditions.

Formulation Procedures

SorC13

SorC13 stock solutions were prepared by dissolving the appropriate amounts of the compound in physiologically buffered saline (pH 7.0 at 25° C.) to comprise a final solution to deliver 300 mg/Kg mouse. Stock solutions were prepared weekly, stored at −20° C. and diluted fresh each day for dosing. All solutions were filter sterilized with a 0.22 mu filter prior to further manipulation. The filter sterilizer units were pre-washed with a small volume of sterile distilled water.

Carboplatin/Paclitaxel (Carboplatin And Taxane: CAT) Reference Solution

Stock solutions were prepared by dissolving the appropriate amounts of the compounds in physiologically buffered saline (pH 7.0 at 25° C.) to comprise final solutions to deliver 60 mg/kg, 40 mg/kg and 20 mg/kg of carboplatin plus 24 mg/kg, 18 mg/kg and 12 mg/kg of paclitaxel, respectively. Carboplatin and paclitaxel was obtained from Sigma-Aldrich. All solutions are filter sterilized with a 0.22 mu filter prior to further manipulation.

Implantation Procedures

To implant SKOV3 tumor cells into NOD/SCID mice, cell cultures were centrifuged to pellet the cells, the supernatant was aspirated, the cell pellet resuspended in 10 ml of growth media and the cell number was determined using a hemocytometer. The cells were then washed in appropriate media and re-suspended at a concentration of $5 \times 10^7$ cells/ml in media. Using a 27-gauge needle and 1 cc syringe, 0.1 ml of the cell suspension was injected subcutaneously into the flanks of the mice. Tumors were then permitted to develop in vivo from subcutaneous injection of cells until the majority reach 50 $mm^3$ in tumor volume, which typically requires 1-2 weeks following cell injection.

Control mice received the saline vehicular control by interperitoneal (i.p.) injection every day for 12 days. A constant dose of SorC13 (300 mg/kg) was used throughout the experiments and injected i.p. every day for 12 days. Low (20 mg/kg carboplatin, 6 mg/kg paclitaxel), medium (40 mg/kg carboplatin, 12 mg/kg paclitaxel) and high (60 mg/kg carboplatin, 24 mg/kg paclitaxel) doses of CAT were injected i.p. on days 1, 4, 8 and 11 as set out in Table 10.

TABLE 10

Treatment doses and injection times for each test group

| Test Group | SorC13 | CAT (carboplatin + paclitaxel) | Injection time |
|---|---|---|---|
| Control (vehicle) | 0 | 0 | Day 1 to 12 |
| SOR-C13 | 300 mg/kg | 0 | Day 1 to 12 |
| Low CAT | 0 | 20 mg/kg carboplatin, 12 mg/kg paclitaxel | Day 1, 4, 8 and 11 |
| Medium | 0 | 40 mg/kg carboplatin, 18 mg/kg paclitaxel | Day 1, 4, 8 and 11 |
| High | 0 | 60 mg/kg carboplatin, 24 mg/kg paclitaxel | Day 1, 4, 8 and 11 |
| SorC13 + Low CAT | 300 mg/kg | 20 mg/kg carboplatin, 12 mg/kg paclitaxel | SorC13 Day 1 to 12; CAT day 1, 4, 8 and 11 |
| SORC13 + Medium CAT | 300 mg/kg | 40 mg/kg carboplatin, 18 mg/kg paclitaxel | SorC13-Day 1 to 12; CAT Day 1, 4, 8 and 11 |
| SOR-C13 + High CAT | 300 mg/kg | 60 mg/kg carboplatin, 24 mg/kg paclitaxel | SOR-C13-Day 1 to 12; CAT-Day 1, 4, 8 and 11 |

Measurements

Animals with oblong, very small or large tumors were discarded, and only animals carrying tumors that displayed consistent growth rates were selected for studies. Tumor volumes (V) were calculated by caliper measurement using standard measurements of the width (W), length (L) and thickness (T) of tumors. Animals were randomized into treatment groups so that the median tumor volumes of each group were similar at the start of dosing. Percentage $\Delta T/\Delta C$ values, as a measure of efficacy, were determined where $\Delta C$ refers to change in volume of control or untreated tumor, and $\Delta T$ refers to change in volume of treated tumor.

Treatment Procedures

Animals were intraperitoneally (i.p.) injected with the vehicular control, or the low, medium or high doses of CAT or CAT and SorC13. Mice received low medium or high doses of CAT or CAT and SorC13 by i.p. injection every day for 12 days or CAT injections as set out in Table 10. Paclitaxel was injected first, followed by carboplatin 30 minutes later and then SorC13. The tumor volume and body weights were measured every day. As well, general health of the animals was monitored every day.

Experimental Results

Figure 13:
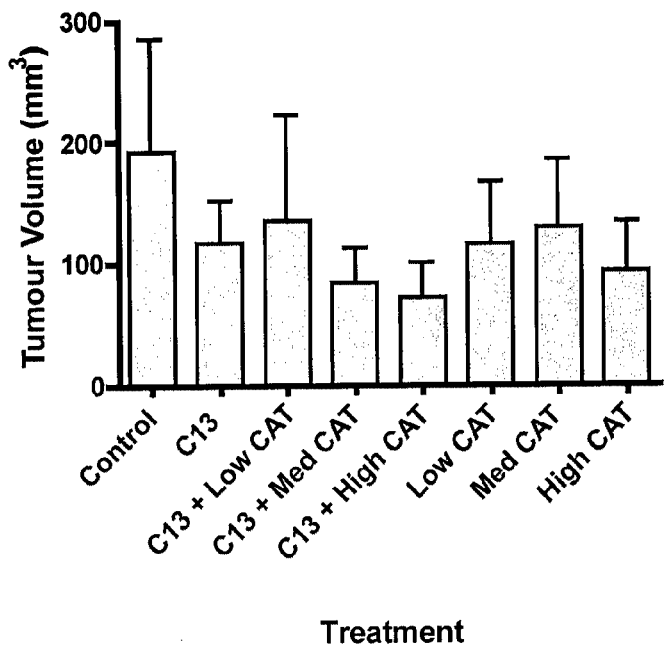
FIG. 13 shows tumour volume in mice with SKOV3 ovarian cancer xenografts at day 12 of treatment with low, medium or high doses of CAT chemotherapy or low, medium or high doses of CAT chemotherapy and SorC13.

FIG. 13 and Table 11 show the mean tumour volume of mice implanted with SKOV3 xenografts at day 12 of treatment with either a control or low medium or high doses of CAT, or low medium or high doses of CAT and SorC13 combination chemotherapy.

TABLE 11

Ovarian SKOV-3 tumor volume in mice at day 12

| Treatment | Mean ($mm^3$) | St. Dev. | N |
|---|---|---|---|
| Control | 191.2 | 93.8 | 20 |
| SorC13 | 116.8 | 33.6 | 20 |
| SorC13 + L | 134.8 | 86.9 | 12 |
| SorC13 + M | 82.8 | 29.4 | 16 |
| SorC13 + H | 72.0 | 27.8 | 16 |
| L | 114.9 | 51.3 | 16 |
| M | 129.2 | 55.3 | 20 |
| H | 92.7 | 40.5 | 19 |

Compared to the control, all tumour volumes from treatment groups with C13 or C13 and CAT were significantly smaller (p<0.0001; students' t-test, 95% confidence level). A low dose of CAT and SorC13 was not statistically different than treatment with a low or medium dose of CAT and resulted in a tumour volume just larger than a high dose of chemotherapy. Mice treated with a medium dose of CAT chemotherapy and the SorC13 peptide had a smaller mean tumour volume than mice treated with a high dose of chemotherapy. Furthermore, treatment with a medium dose of CAT chemotherapy and the SorC13 peptide was more effective than treatment with a medium dose of CAT chemotherapy alone. The combined high dose of CAT and SorC13 had the smallest mean tumour volume but was not a statistically significantly different from treatment with a high dose of CAT alone (p=0.09; students' t-test, 95% confidence level).

Figure 14:
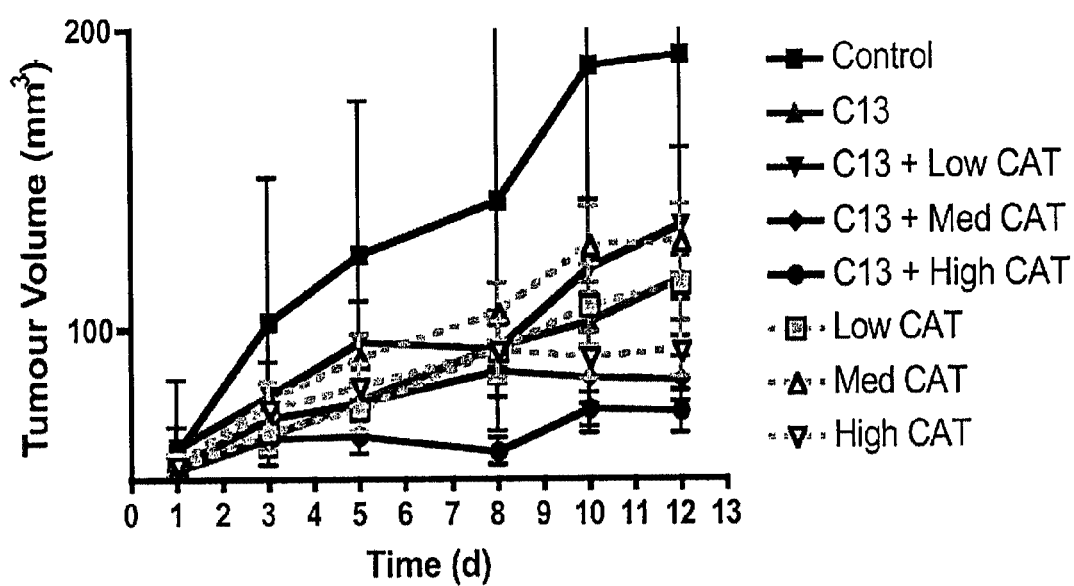
FIG. 14 shows tumour volume in mice with SKOV3 ovarian cancer xenografts over 12 days of treatment with low, medium or high doses of CAT chemotherapy or low, medium or high doses of CAT chemotherapy and SorC13.

FIG. 14 shows the time course results of tumour volume measured each day for 12 days. Table 12 also shows that at day 12, the normalized tumour volume for mice treated with SorC13 and a high or medium dose of CAT was lower than for mice treated with a high dose of CAT chemotherapy alone.

TABLE 12

SKOV-3 ovarian cancer tumour volume normalized to control volume at day 12 of treatment.

| Treatment | % ΔT/ΔC |
|---|---|
| Control | 100.0 |
| C13 | 47.6 |
| C13 + L | 56.6 |
| C13 + M | 21.8 |
| C13 + H | 14.3 |
| L | 46.3 |
| M | 56.6 |
| H | 29.3 |

Example 27

Anti-Tumor Activity of SorC13 in Combination with Paclitaxel Against Breast Cancer Tumor Cells (T-47D) in a Mouse Xenograft Model T-47D Cell Line The human ovarian breast cancer cell line T-47D (ATCC #HTB-133), was cultured in growth media prepared with ATCC complete growth medium. The base medium for the T-47D cell line is ATCC-formulated RPMI-1640 Medium. The complete growth medium is supplemented with 0.2 Units/ml bovine insulin and fetal bovine serum to a final concentration of 10% (v/v). Cells were cultured at 37° C. in an atmosphere of 95% air and 5% carbon dioxide with subculturing done according to ATCC guidelines.

The cell preparation, formulation, implantation, measurement and treatment procedures were otherwise as described in Example 26 and Table 10 but with Paclitaxel at low (6 mg/kg), medium (10 mg/kg) and high (16 mg/kg) doses.

Experimental Results

FIG. 14 and Table 13 show the mean tumour volume of mice implanted with T 47D xenografts at day 12 of treatment with either a control or low medium or high doses of Paclitaxel, or low medium or high doses of Paclitaxel and SorC13 combination chemotherapy.

TABLE 13

T47D breast cancer tumor volume in mice at day 12 of treatment

| | 12-day treatment | |
|---|---|---|
| Treatment | Mean (mm³) | SD |
| Control | 60.58 | 32.02 |
| SOR-C13 | 43.61 | 22.75 |
| SOR-C13 + Low | 34.67 | 26.28 |
| SOR-C13 + Med | 33.08 | 18.53 |
| SOR-C13 + High | 20.29 | 16.90 |
| Low | 46.37 | 28.14 |
| Med | 36.23 | 15.21 |
| High | 26.47 | 19.22 |

Treatment with SorC13 alone was as effective as low and medium doses of Paclitaxel chemotherapy in reducing tumour volume. Treatment with SorC13 in combination with a low dose of Paclitaxel was not statistically different from treatment with a low, medium or high dose of Paclitaxel chemotherapy. Furthermore, treatment with a combination of SorC13 with either a medium or high dose of Paclitaxel resulted in lower mean tumour volumes, than treatment with medium or high doses of Paclitaxel respectively. The lowest mean tumour volume was seen with a combination of SorC13 and a high dose of Paclitaxel chemotherapy.

Figure 15:
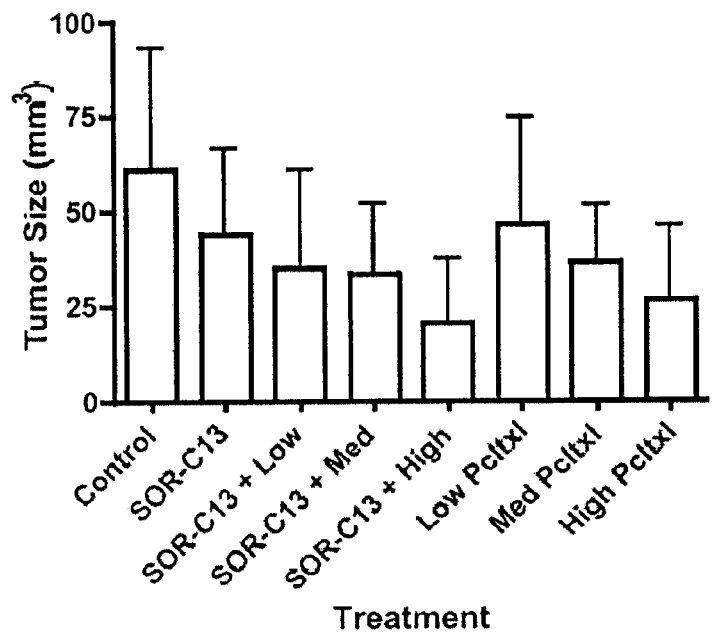
FIG. 15 shows tumour volume in mice with T47D breast cancer xenografts at day 12 of treatment with low, medium or high doses of Paclitaxel chemotherapy or low, medium or high doses of Paclitaxel chemotherapy and SorC13.

Tumour volumes in mice were also evaluated 12 days after the termination of treatment with either Paclitaxel or a combination of SorC3 and Paclitaxel to evaluate the persistence of the chemotherapeutic effect as shown in FIG. 15 and Table 14.

TABLE 14

T-47D breast cancer tumour volumes after a 12-day rest post-treatment.

| | 12-day rest | | |
|---|---|---|---|
| Treatment | Mean (mm³) | SD | N |
| Control | 69.15 | 50.43 | 13 |
| SOR-C13 | 55.76 | 33.42 | 16 |
| SOR-C13 + Low | 39.83 | 31.24 | 14 |
| SOR-C13 + Med | 23.26 | 11.03 | 14 |
| SOR-C13 + High | 10.49 | 7.73 | 16 |
| Low | 52.08 | 35.02 | 14 |
| Med | 35.52 | 13.31 | 15 |
| High | 20.24 | 14.01 | 14 |

Remarkably, 12 days after the end of treatment mice that received the combination of SorC13 and high dose Paclitaxel chemotherapy showed a statistically significant lower tumour volume than mice treated only with a high dose of Paclitaxel chemotherapy (p=0.0237; students' t-test, 95% confidence level). Furthermore, mice treated with a combination of SorC13 and a medium dose of Paclitaxel chemotherapy did not show a statistically significant difference in tumour volume compared to mice that had received a high dose of Paclitaxel chemotherapy (p=0.5205; students' t-test, 95% confidence level), but did show an improvement over mice treated with a medium dose of Paclitaxel chemotherapy alone (p=0.0124; students' t-test, 95% confidence level).

Figure 16:
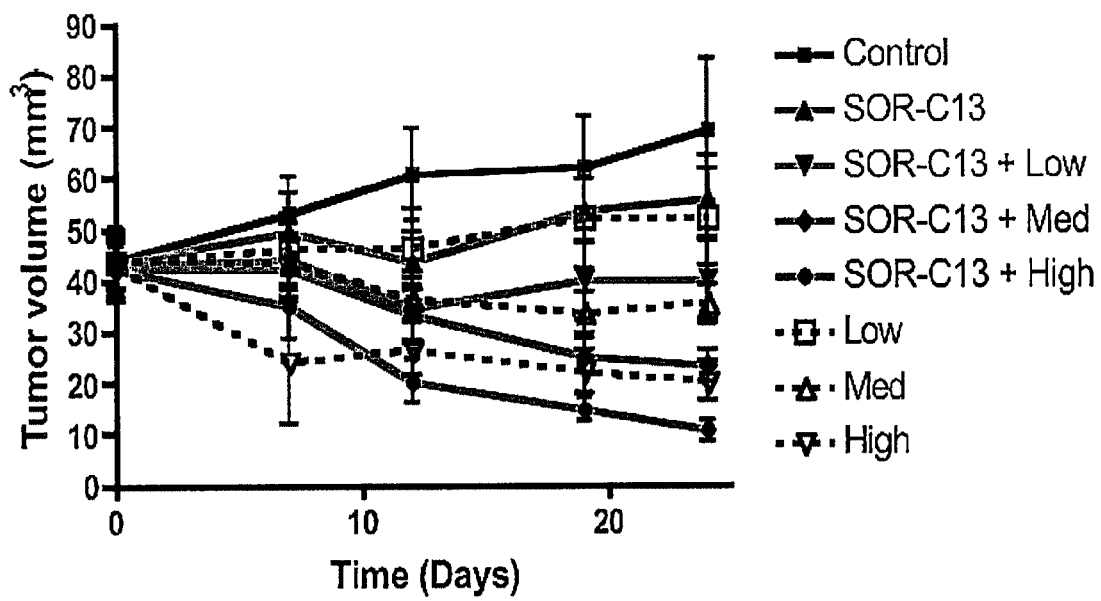
FIG. 16 shows tumour volume in mice with T47D breast cancer xenografts over 24 days of treatment with low, medium or high doses of Paclitaxel chemotherapy or low, medium or high doses of Paclitaxel chemotherapy and SorC13.

FIG. 16 shows the tumor volumes over a time-course of a 12-day treatment and a 12-day recovery for mice treated with SorC13 with or without low, medium or high doses of Paclitaxel chemotherapy. For mice treated with a combination of Paclitaxel chemotherapy and SorC13 tumour shrinkage and not just a decrease in the rate of growth was observed. Additionally, the anti-tumour effects extended into the 12-day recovery period where there was no treatment. The shrinkage in tumour volume is readily observed in FIG. 17 and Table 15, which show the relative change compared to the control (%ΔT/ΔC) for each of the different treatments.

TABLE 15

T47-D breast cancer tumor volumes normalized to control after 12-days rest for each treatment group

| Treatment | Day 6 | Day 12 | Day 18 | Day 24 |
|---|---|---|---|---|
| Control | 100 | 100 | 100 | 100 |
| C13 | 66.0 | 1.0 | 54.5 | 48.7 |
| C13 + L | 11.8 | −49.3 | −16.3 | −12.3 |
| C13 + M | 1.5 | −54.3 | −93.0 | −74.8 |
| C13 + H | −80.1 | −130.5 | −150.8 | −125.1 |
| Low | 26.0 | 16.3 | 46.0 | 33.3 |
| Medium | −4.0 | −45.9 | −56.9 | −33.2 |
| High | 17.8 | −96.4 | −112.4 | −88.4 |

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

Agnes, R. S., Lee, Y. S., Davis, P., Ma, S. W., Badghisi, H., Porreca, F., Lai, J., and Hruby, V. J. 2006. Structure-activity relationships of bifunctional peptides based on overlapping parmacophores and opioid and cholescytokinin receptors. Journal of Medicinal Chemistry, 49: 2868-2875.

Peng, J., Zhuang, L., Berger, U. V., Adam, R. M., Williams, B. J., Brown, E. M., Hediger, M. A. and Freeman, M. R. 2001. CaT1 expression correlates with tumor grade in prostate cancer. [note: CaT1 is now called TRPV6.]

Pigozzi, D., Ducret, T., Tajeddine, N., Gala, J. L., Tombai, B. and Gailly, P. 2006, Calcium store contents control the expression of TRPC1, TRPC3 and TRPV6 in LnCaP prostate cancer cell line. Cell Calcium, 39: 401-415.

Yamamoto, T., Nair, P. Vagner, J., Largent-Milnes, T. Davis, P., Ma, S. W., Navratilova, E., Moye, S., Tumati, S., Lai, J., Yamamura, H. I., Vanderah, T. W., Porreca, F., and Hruby, V. J. 2008. A structure-activity relationship study of combinatorial synthetic approach of C-terminal modified bifunctional peptides that are delt/mu opioid receptor agonists and neurokinin 1 receptor antagonists. Journal of Medicinal Chemistry, epub, 12 Feb.

Zhuang, L., Peng, J., Tou, L., Takanaga, H., Adam, R. M. Hediger, M. A. and Freeman, M. R. 2002. Calcium-selective ion channel, CaT1, is apically localized in gastrointestinal tract epithelia and is aberrantly expressed in human malignancies. Laboratory Investigation, 82: 1755-1764. [note: CaT1 is now called TRPV6.]

Lyshchik A, Higashi T, Asato R, Tanaka S, Ito J, Hiraoka M, Insana M F, Brill A B, Saga T, Togashi K. Cervical lymph node metastases: diagnosis at sonoelastography—initial experience. Radiology. 2007 April; 243(1):258-67. Epub 2007 Feb. 9.

Vernooij F, Sie-Go D M, Heintz A P. Lymph node recurrence following stage 1A vulvar carcinoma: two cases and a short overview of literature. Int J Gynecol Cancer. 2007 March-April; 17(2):517-20. Epub 2007 Feb. 19. Review.

Aalders J G, Thomas G. Endometrial cancer—revisiting the importance of pelvic and para aortic lymph nodes. Gynecol Oncol. 2007 January; 104(1):222-31. Epub 2006 Nov. 28. Review Veness M J, Porceddu S, Palme C E, Morgan G J. Cutaneous head and neck squamous cell carcinoma metastatic to parotid and cervical lymph nodes. Head Neck. 2007 July; 29(7):621-31. Review.

Ma J, Liu L, Tang L, Zong J, Lin A, Lu T, Cui N, Cui C, Li L. Retropharyngeal lymph node metastasis in nasopharyngeal carcinoma: prognostic value and staging categories. Clin Cancer Res. 2007 Mar. 1; 13(5):1445-52.

Mujoomdar A, Austin J H, Malhotra R, Powell C A, Pearson G D, Shiau M C, Raftopoulos H. Clinical predictors of metastatic disease to the brain from non-small cell lung carcinoma: primary tumor size, cell type, and lymph node metastases. Radiology. 2007 March; 242(3):882-8. Epub 2007 Jan. 17.

Wind J, Lagarde S M, Ten Kate F J, Ubbink D T, Bemelman W A, van Lanschot J J. A systematic review on the significance of extracapsular lymph node involvement in gastrointestinal malignancies. Eur J Surg Oncol. 2007 May; 33(4):401-8. Epub 2006 Dec. 15. Review.

Mujoomdar A, Austin J H, Malhotra R, Powell C A, Pearson G D, Shiau M C, Raftopoulos H. Clinical predictors of metastatic disease to the brain from non-small cell lung carcinoma: primary tumor size, cell type, and lymph node metastases. Radiology. 2007 March; 242(3):882-8. Epub 2007 Jan. 17.

Lehen'kyi V, Flourakis M, Skryma R, Prevarskaya N. TRPV6 channel controls prostate cancer cell proliferation via Ca2+/NFAT-dependent pathways. Oncogene. 2007. 26: 7380-7385.

Bolanz K A, Hediger M A, Landowski C P. The role of TRPV6 in breast carcinogenesis. Molecular Cancer Therapy. 2008. 7(2): 271-279.

Bodding M, Fecher-Trost C, Flockerzi V. Store-operated $Ca^{2+}$ Current and TRPV6 Channels in Lymph Node Prostate Cancer Cells. J Biol. Chem. 2003. 278 (51): 50872-50879.

I claim:

1. An isolated peptide consisting of (i) the amino acid sequence set forth in SEQ ID NO: 1 or (ii) the amino acid residues at positions 15 to 27 of SEQ ID NO: 1, wherein the peptide inhibits calcium channel activity without paralytic activity.

2. The peptide of claim 1, wherein the calcium channel comprises a TRPV6 calcium channel.

3. A pharmaceutical composition comprising the peptide of claim 1 and a carrier.

4. The pharmaceutical composition of claim 3, further comprising a chemotherapeutic agent.

5. The pharmaceutical composition of claim 4, wherein the chemotherapeutic agent is paclitaxel or carboplatin.

6. The pharmaceutical composition of claim 3, wherein the carrier is a pharmaceutically acceptable vehicle or diluent.

* * * * *

SEQUENCE LISTING

<160> NUMBER OF SEQ ID NOS: 2

<210> SEQ ID NO 1
<211> LENGTH: 27
<212> TYPE: PRT
<213> ORGANISM: Artificial Sequence
<220> FEATURE:
<223> OTHER INFORMATION: Synthetic construct

```
<400> SEQUENCE: 1

Glu Gly Lys Leu Ser Ser Asn Asp Thr Glu Gly Gly Leu Cys Lys Glu
1               5                   10                  15

Phe Leu His Pro Ser Lys Val Asp Leu Pro Arg
            20                  25

<210> SEQ ID NO 2
<211> LENGTH: 18
<212> TYPE: PRT
<213> ORGANISM: Artificial Sequence
<220> FEATURE:
<223> OTHER INFORMATION: Synthetic construct

<400> SEQUENCE: 2

Ser Ile Leu Ala Arg Pro Ala Glu Leu Asn Thr Glu Thr Cys Ile Leu
1               5                   10                  15

Glu Cys
```